United States Patent
Ko et al.

(10) Patent No.: US 11,510,948 B2
(45) Date of Patent: Nov. 29, 2022

(54) COMPOSITION FOR DIAGNOSIS AND TREATMENT OF ALCOHOLIC LIVER DISEASE, USING CHANGE IN SHORT-CHAIN FATTY ACID PRODUCING GUT BACTERIAL COMMUNITY

(71) Applicant: KoBioLabs, Inc., Seoul (KR)

(72) Inventors: Gwangpyo Ko, Seoul (KR); Boram Seo, Seoul (KR); Woon Ki Kim, Ulsan (KR); Kyungchan Jeon, Uijeongbu-si (KR)

(73) Assignee: KOBIOLABS, INC., Seoul (KR)

( * ) Notice: Subject to any disclaimer, the term of this patent is extended or adjusted under 35 U.S.C. 154(b) by 183 days.

(21) Appl. No.: 16/648,358

(22) PCT Filed: Sep. 28, 2018

(86) PCT No.: PCT/KR2018/011564
§ 371 (c)(1),
(2) Date: Mar. 18, 2020

(87) PCT Pub. No.: WO2019/066577
PCT Pub. Date: Apr. 4, 2019

(65) Prior Publication Data
US 2021/0052674 A1 Feb. 25, 2021

(30) Foreign Application Priority Data
Sep. 28, 2017 (KR) .......... 10-2017-0126557
Sep. 28, 2018 (KR) .......... 10-2017-0115823

(51) Int. Cl.
| | | |
|---|---|---|
| A61K 35/741 | (2015.01) | |
| A61K 39/02 | (2006.01) | |
| A61K 35/00 | (2006.01) | |
| A23L 33/135 | (2016.01) | |

(52) U.S. Cl.
CPC .......... *A61K 35/741* (2013.01); *A23L 33/135* (2016.08); *A61K 39/0208* (2013.01); *A61K 2035/115* (2013.01)

(58) Field of Classification Search
None
See application file for complete search history.

(56) References Cited

U.S. PATENT DOCUMENTS

| 9,758,838 B2 | 9/2017 | Flavell et al. | |
|---|---|---|---|
| 2014/0363397 A1* | 12/2014 | Allen-Vercoe | A61P 29/00 |
| | | | 424/93.3 |
| 2015/0071957 A1 | 3/2015 | Kelly et al. | |
| 2021/0008128 A1* | 1/2021 | Nandakumar | A61K 35/74 |

FOREIGN PATENT DOCUMENTS

| KR | 10-2017-0032848 | 3/2017 |
|---|---|---|
| WO | 2014167338 | 10/2014 |
| WO | 2016/172658 | 10/2016 |
| WO | 2017/042347 | 3/2017 |

OTHER PUBLICATIONS

New Riverside University Dictionary, The Riverside Publishing Company, p. 933, 1984.*
Gladys Ferrere et al., "Fecal microbiota manipulation prevents dysbiosis and alcohol-induced liver injury in mice", Journal of Hepatology, Elsevier, Amsterdam, NL, (Nov. 25, 2016), vol. 66, No. 4, pp. 806-815.
Zohreh Tamanai-Shacoori et al., "*Roseburia* spp.: a marker of health?", Future Microbiology, GB, (Feb. 1, 2017), vol. 12, No. 2, pp. 157-170.
V. B. Dubinkina et al., "Metagenomic analysis of taxonomic and functional changes in gut microbiota of patients with the alcohol dependence syndrome", Biochemistry (Moscow). Supplement Series B: Biomedical Chemistry, Maik Nauka—Interperiodica, RU, vol. 10, No. 2, pp. 184-190.
EPO, European search report of EP 18860264.3 dated May 21, 2021.
Anja S. Hummel et al., "Antibiotic Resistances of Starter and Probiotic Strains of Lactic Acid Bacteria", Applied and Environmental Microbiology, Feb. 2007, vol. 73, No. 3, p. 730-739. doi:10.1128/AEM.02105-06.
KIPO, PCT Search Report & Written Opinion of PCT/KR2018/011564 dated Apr. 10, 2019.
Zohreh Tamanai-Shacoori et al., "*Roseburia* spp.: a marker of health?", Future Microbiol. (2017) 12(2), 157-170.
Allison Clark et al., "The Crosstalk between the Gut Microbiota and Mitochondria during Exercise", Frontiers in Physiology, vol. 8, May 2017.
E. Lau et al., "Gut Microbiota: Association with NAFLD and Metabolic Disturbances", BioMed Research International, vol. 2015. http://dx.doi.org/10.1155/2015/979515.
Makoto Usami et al., "Gut microbiota and host metabolism in liver cirrhosis", World J Gastroenterol Nov. 7, 2015; 21(41): 11597-11608.

* cited by examiner

*Primary Examiner* — S. Devi
(74) *Attorney, Agent, or Firm* — Lex IP Meister, PLLC

(57) ABSTRACT

The present invention relates to a microorganism which can act as a biomarker of alcoholic fatty liver disease, and relates to a pharmaceutical composition for preventing or treating alcoholic fatty liver disease, a food composition for preventing or improving alcoholic fatty liver disease, or a probiotics composition for preventing or improving alcoholic fatty liver disease, comprising the strain as an active ingredient.

11 Claims, 30 Drawing Sheets
Specification includes a Sequence Listing.

[FIG. 1]
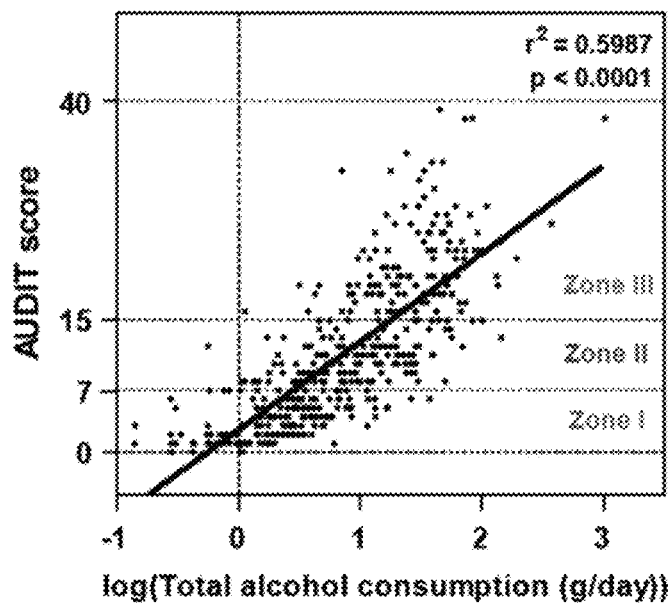
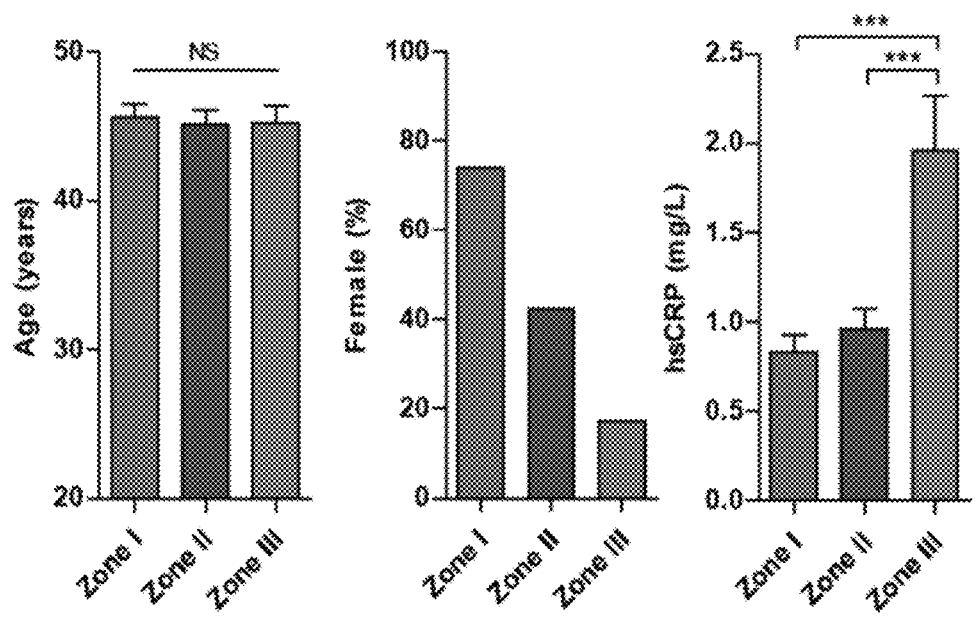

[FIG. 2]
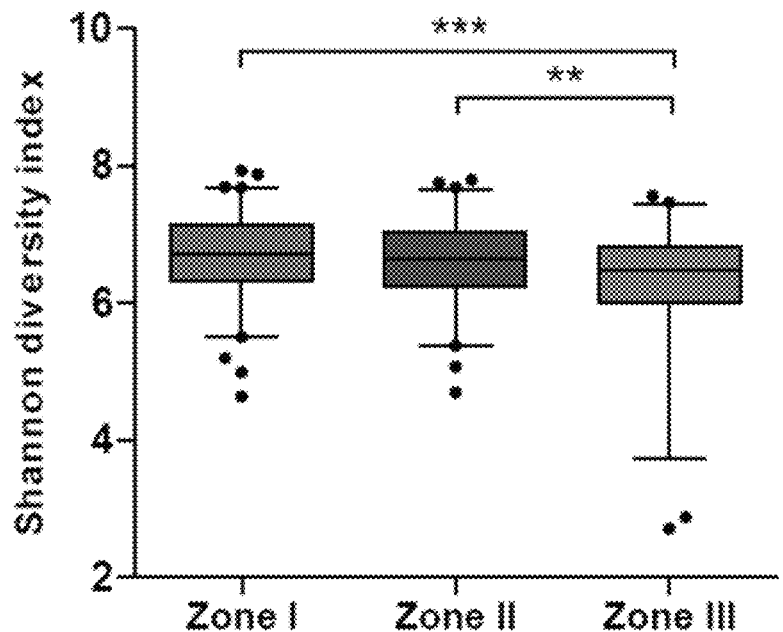
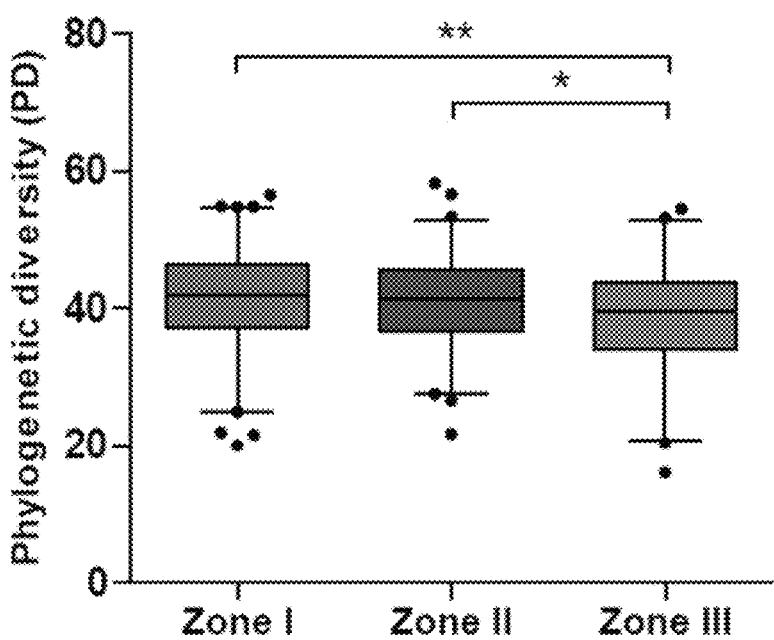

[FIG. 3]
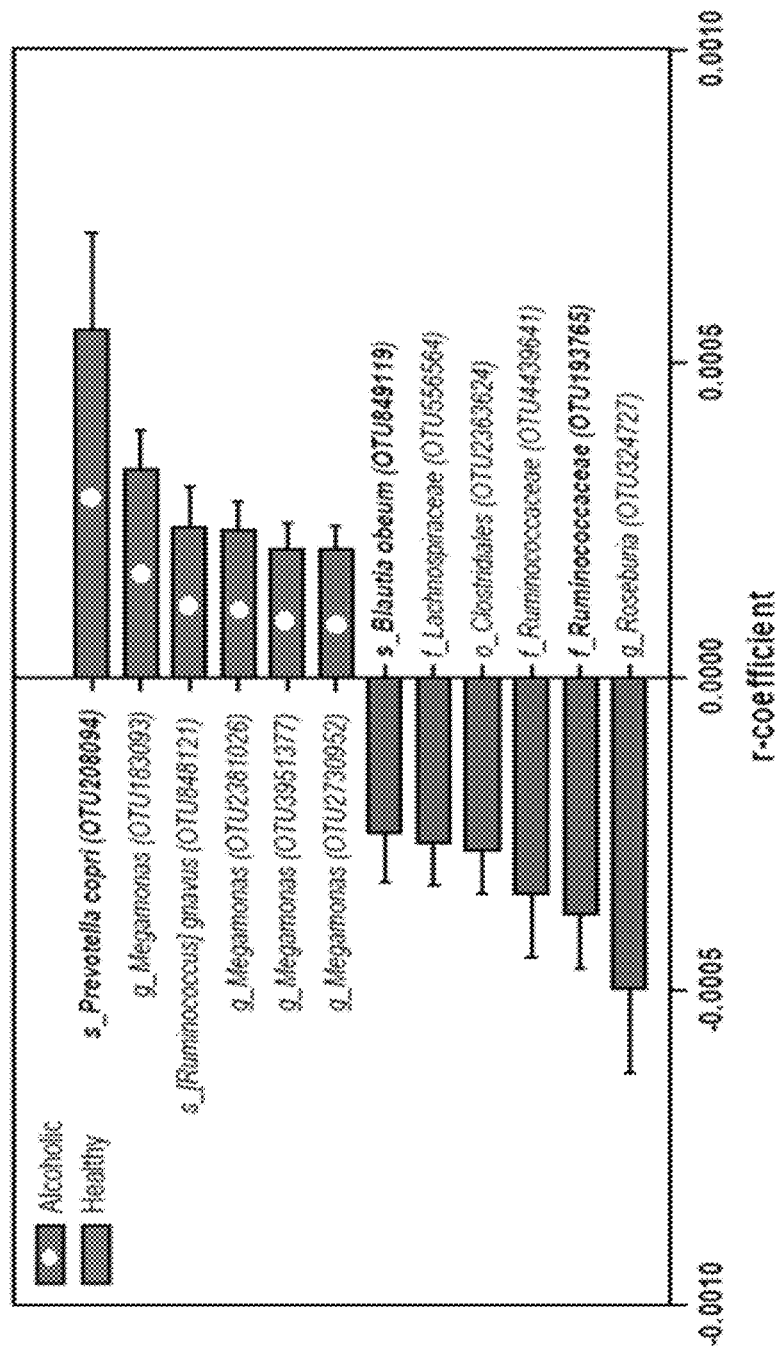

[FIG. 4]
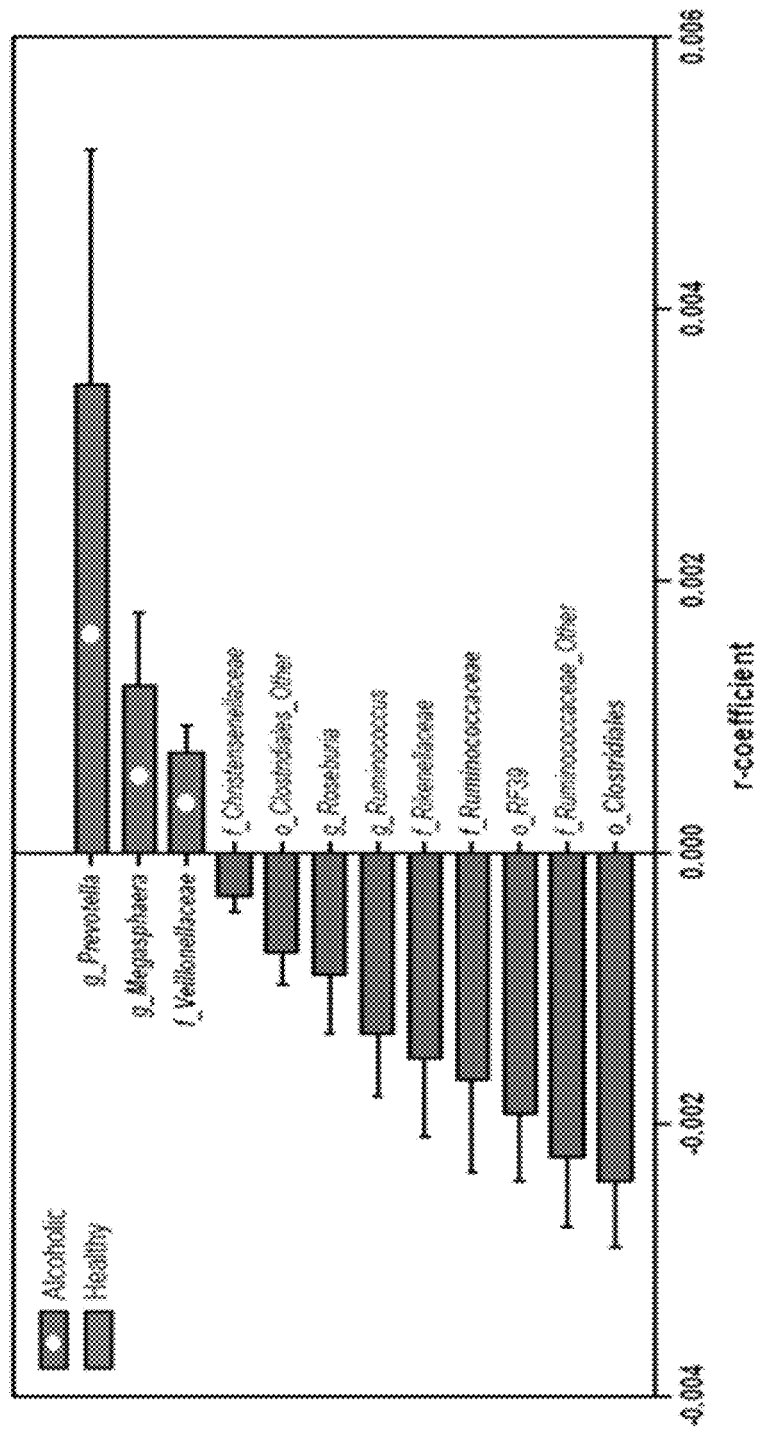

[FIG. 5]
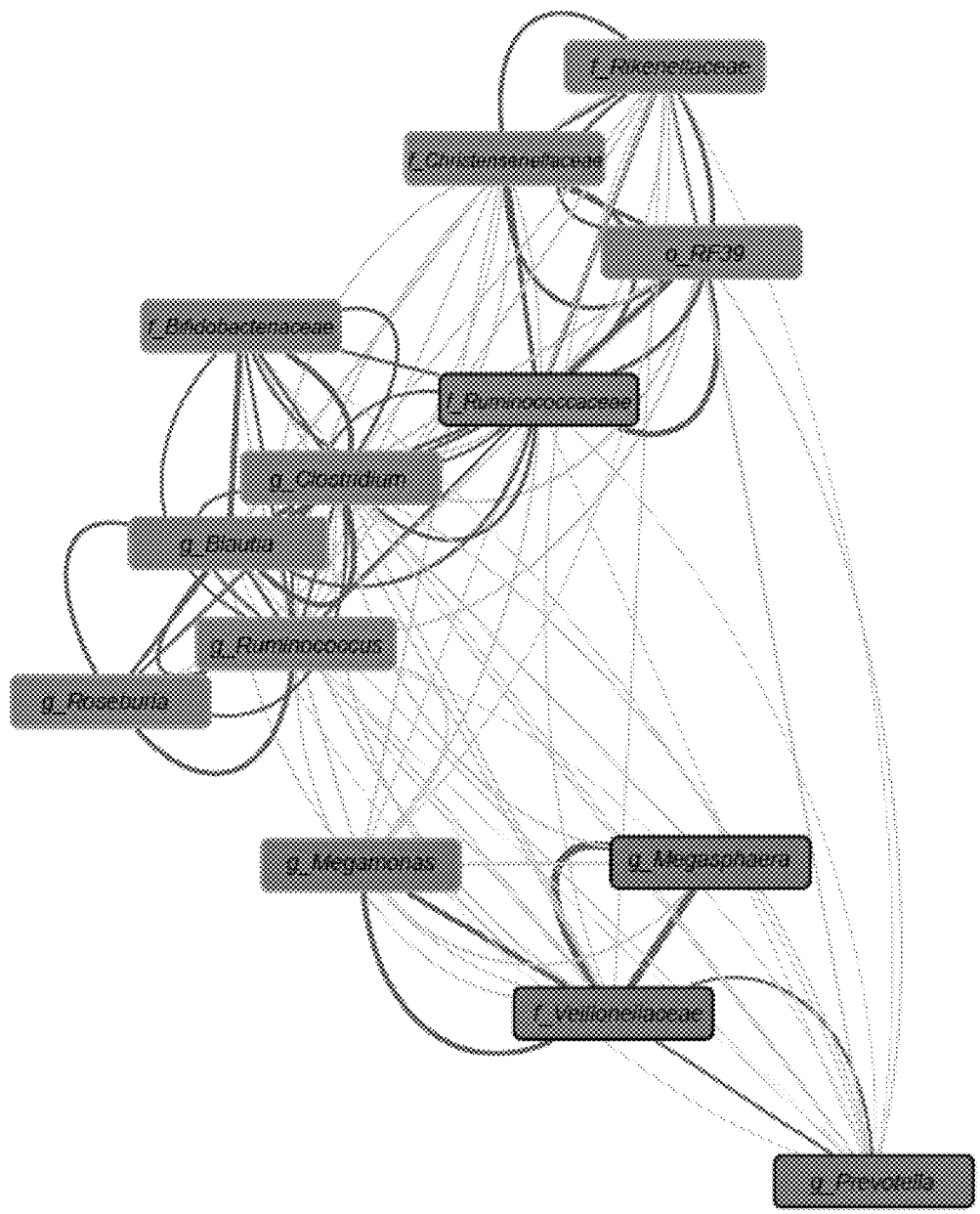

[FIG. 6]
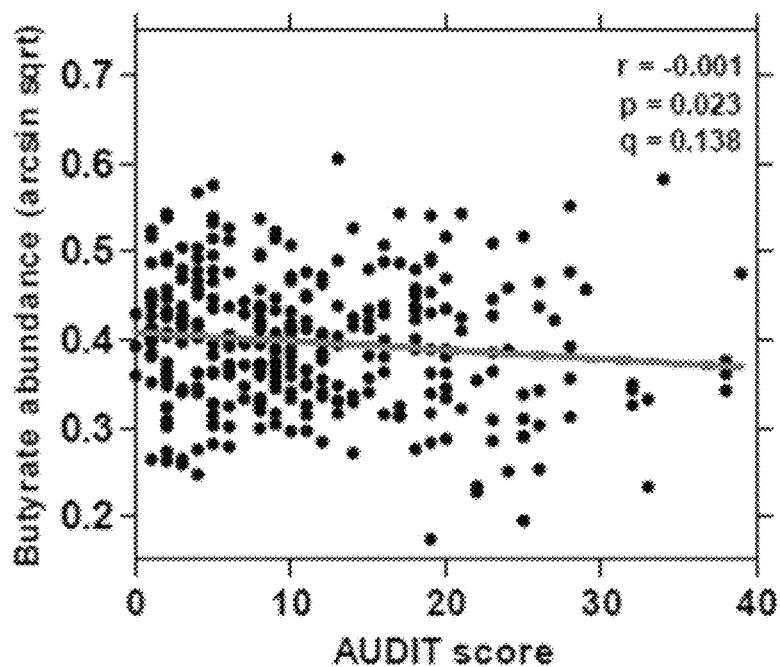
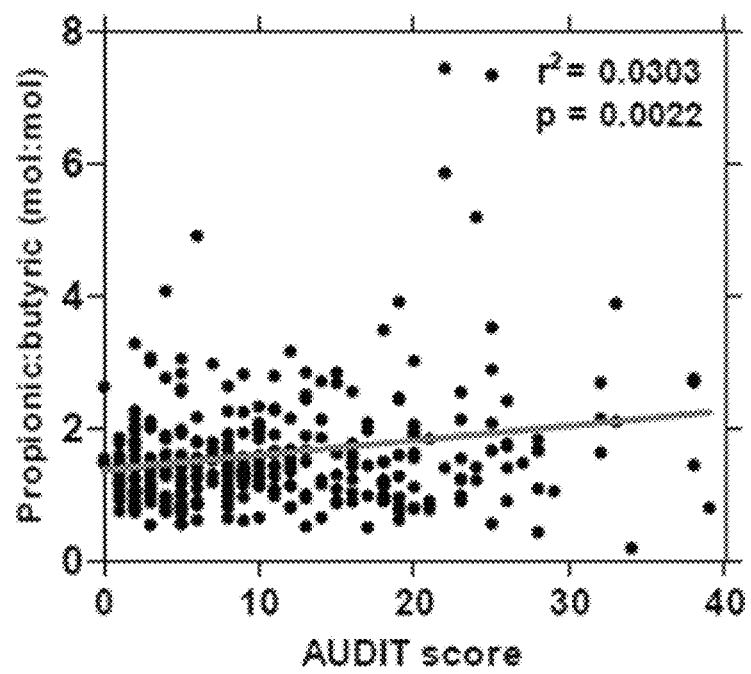

[FIG. 7]
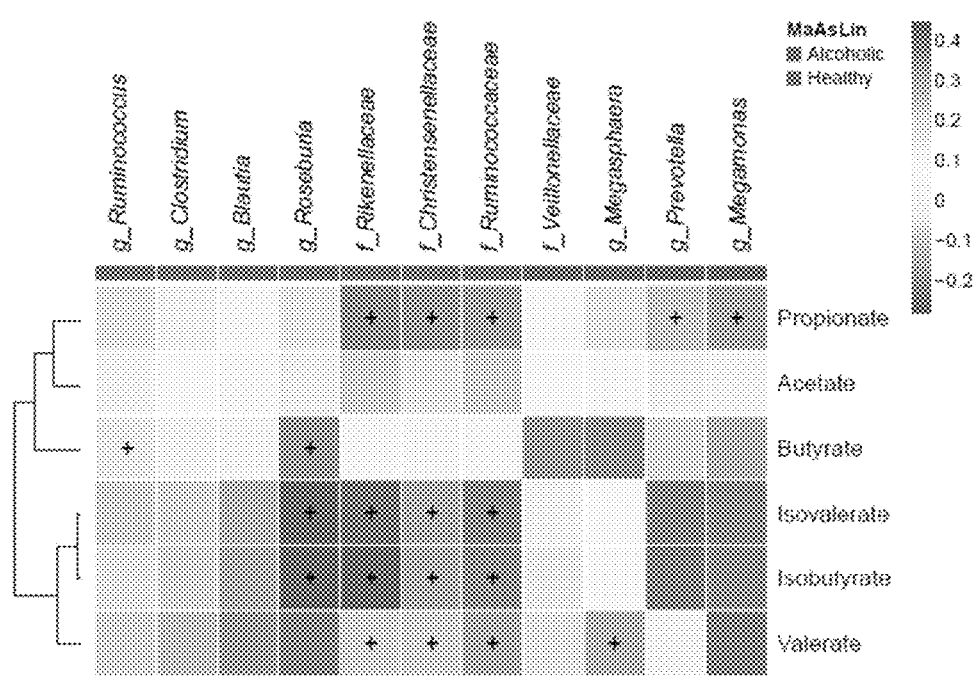

[FIG. 8a]
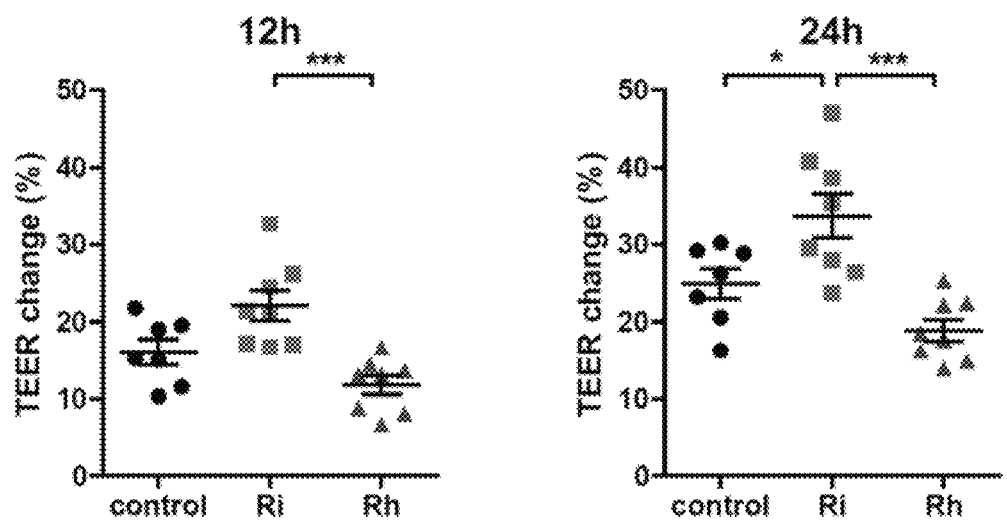

[FIG. 8b]
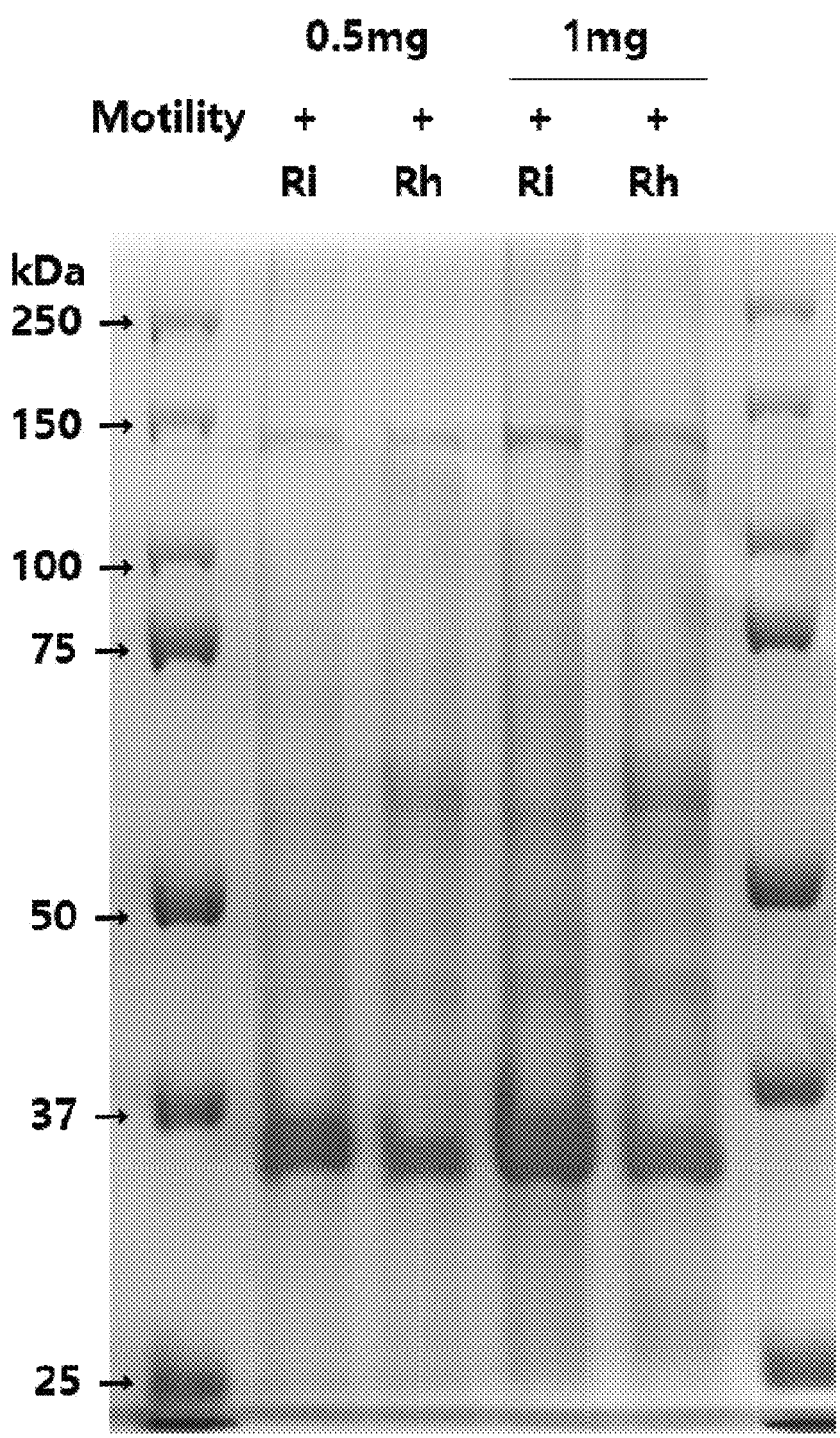

| Accession | Coverage | MW [kDa] | calc. pI | Score | Description |
|---|---|---|---|---|---|
| Q5LBI4450 | 61.85 | 28.6 | 5.41 | 1046.55 | Flagellin [Roseburia hominis] |

Ri

| Accession | Coverage | MW [kDa] | calc. pI | Score | Description |
|---|---|---|---|---|---|
| Q2I5J9853 | 42.27 | 30.7 | 5.26 | 1067.00 | Flagellin and related hook-associated proteins [Roseburia intestinalis M50/1] |
| Q4R81945 | 43.30 | 29.0 | 5.39 | 651.89 | Flagellin [Roseburia intestinalis] |
| Q2I5J9847 | 24.92 | 27.9 | 5.47 | 535.18 | Flagellin and related hook-associated proteins [Roseburia intestinalis 1085B] |
| Q5LBI4360 | 37.70 | 28.6 | 5.42 | 268.65 | Flagellin [Roseburia hominis] |
| Q2I5J7706 | 7.95 | 56.3 | 4.65 | 135.55 | Flagellin and related hook-associated proteins [Roseburia intestinalis M50/1] |

[FIG. 8d]
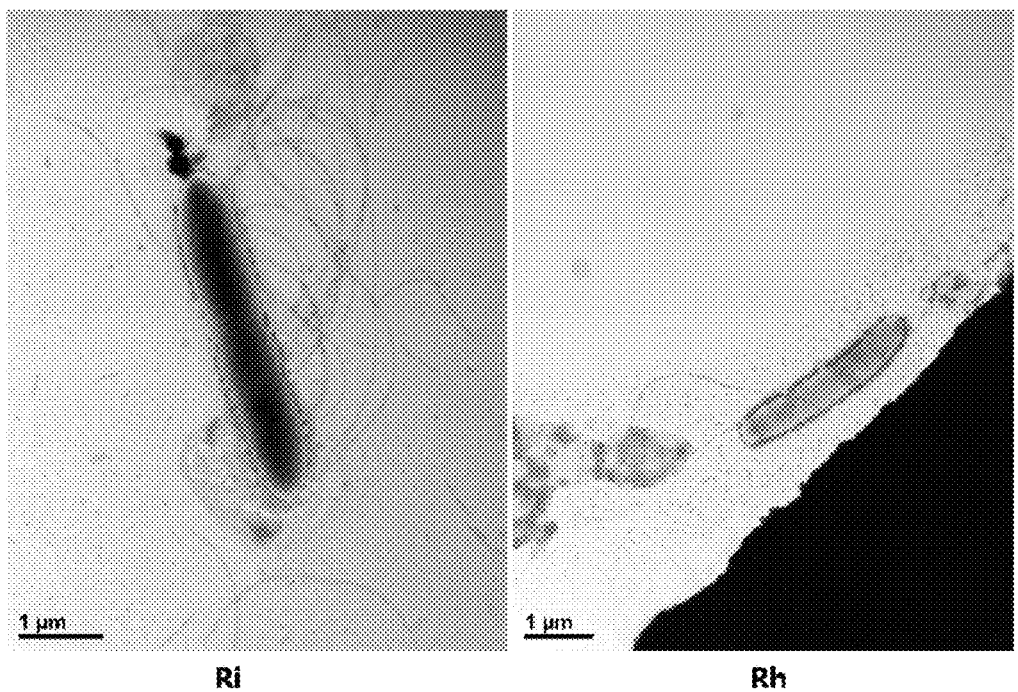

[FIG. 8e]
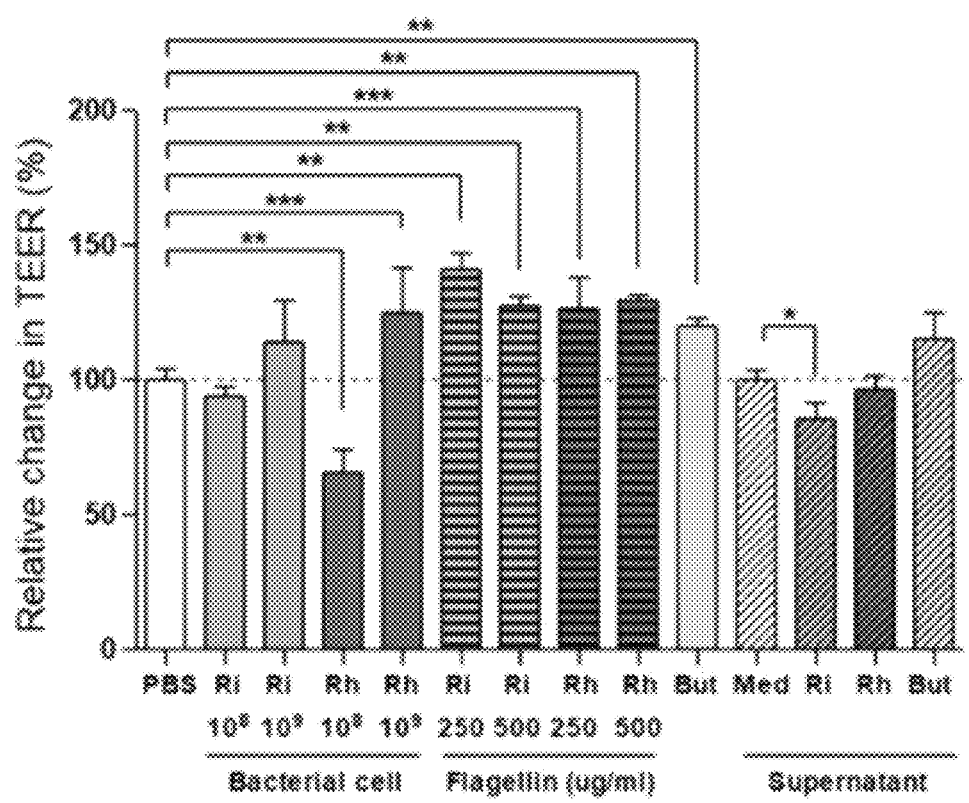

[FIG. 8f]
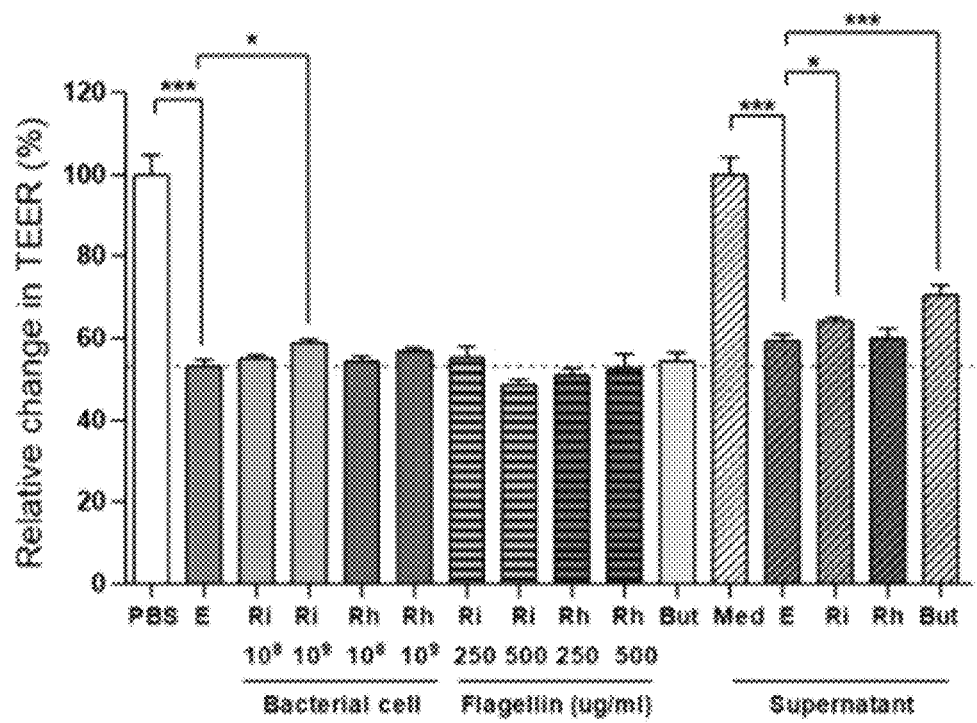

[FIG. 8g]
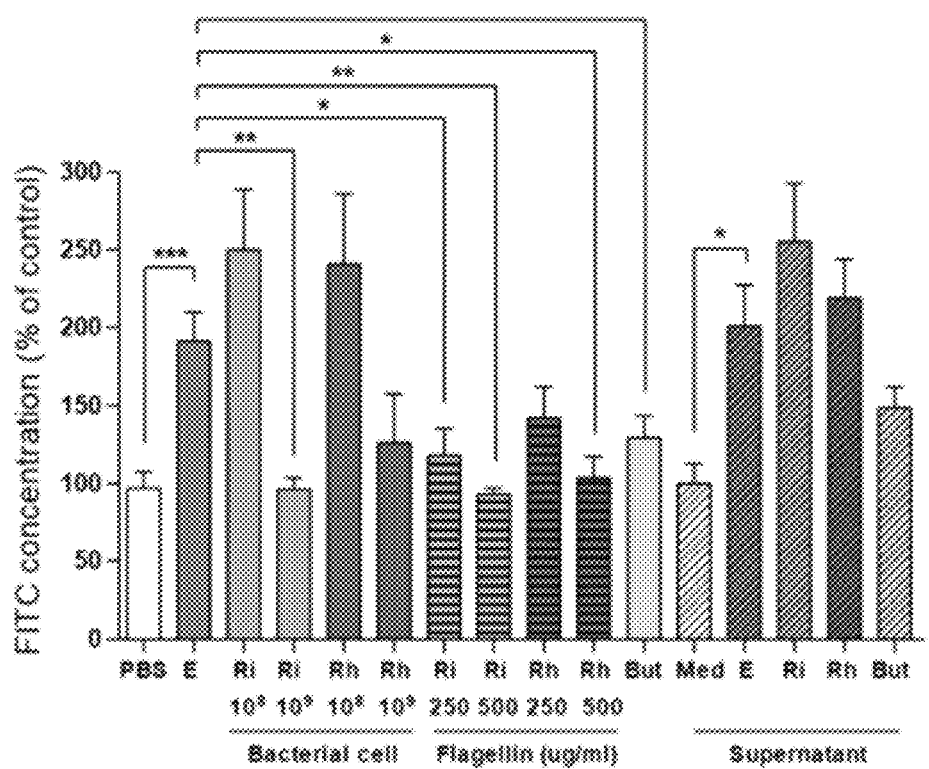

[FIG. 9a]
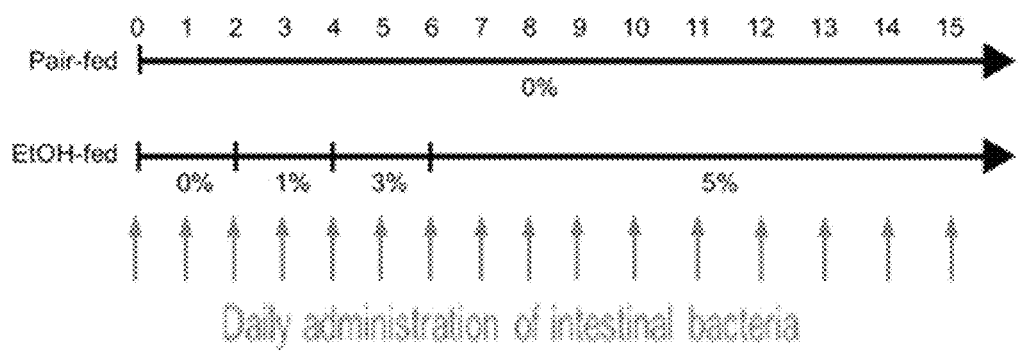

[FIG. 9b]
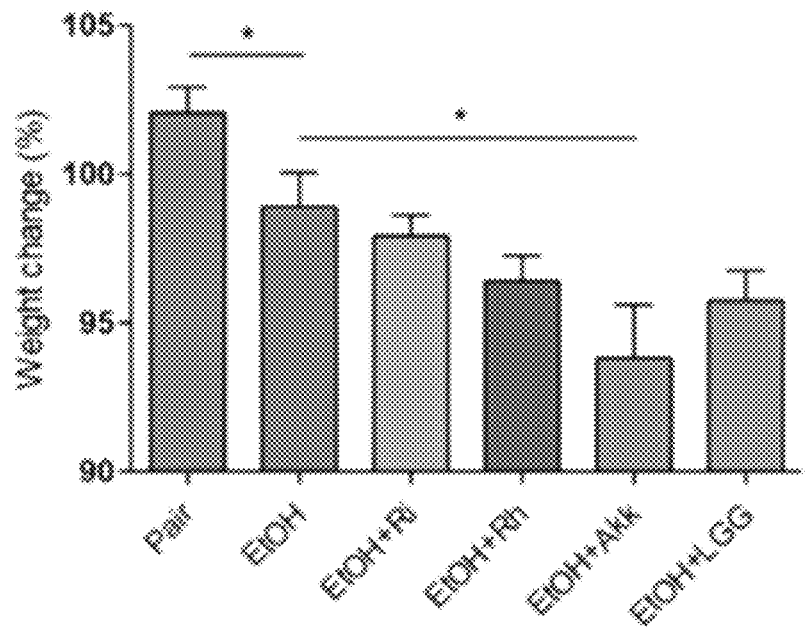
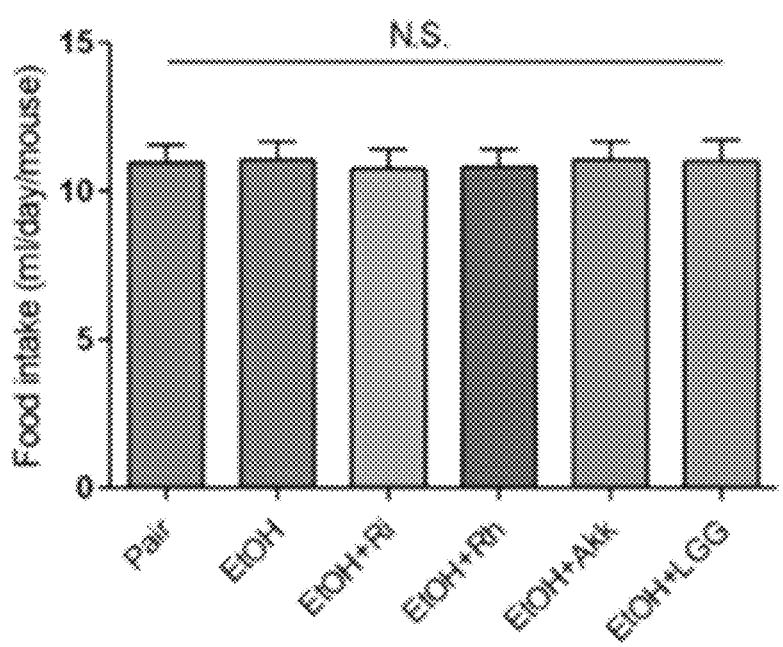

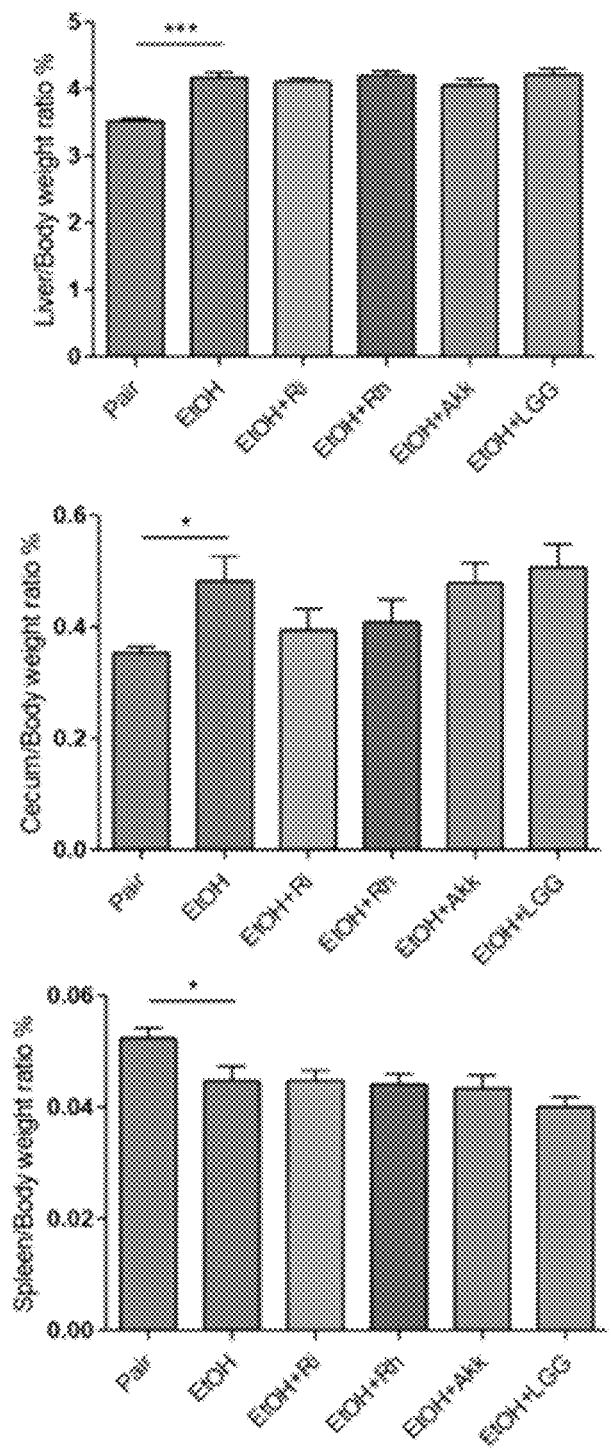
[FIG. 10]

[FIG. 11]
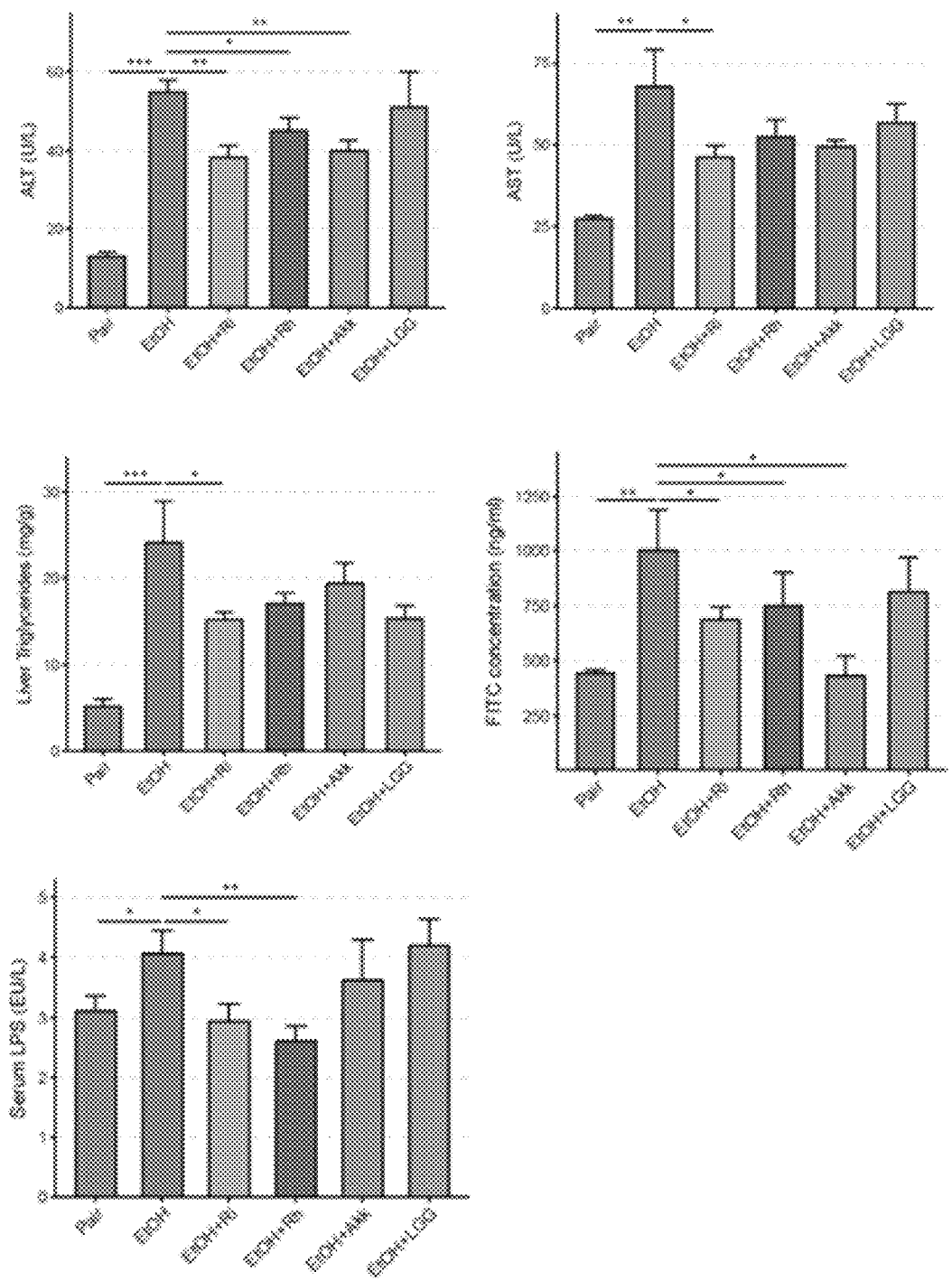

[FIG. 12]
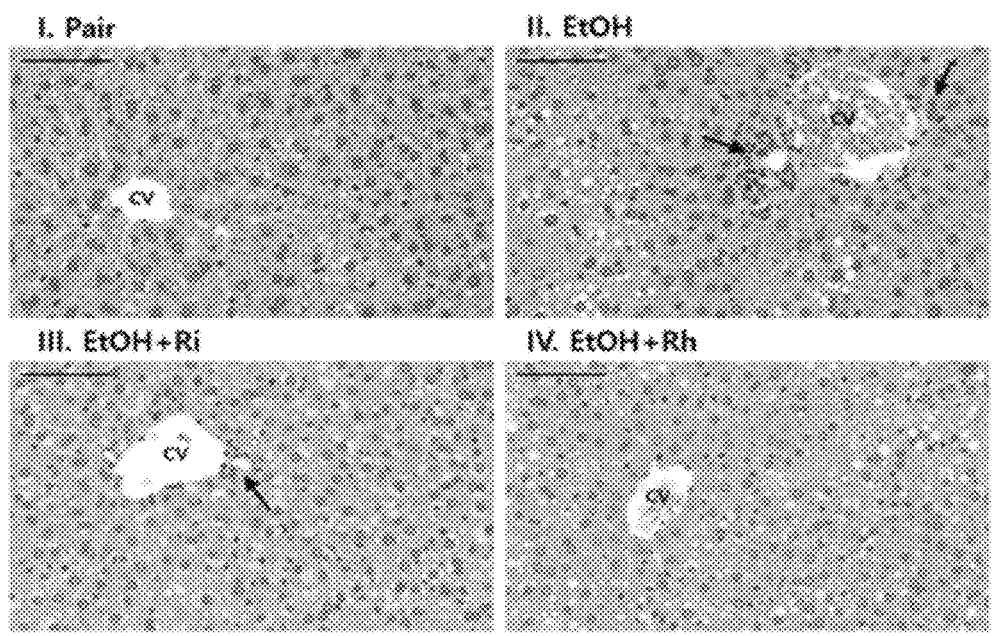

[FIG. 13a]
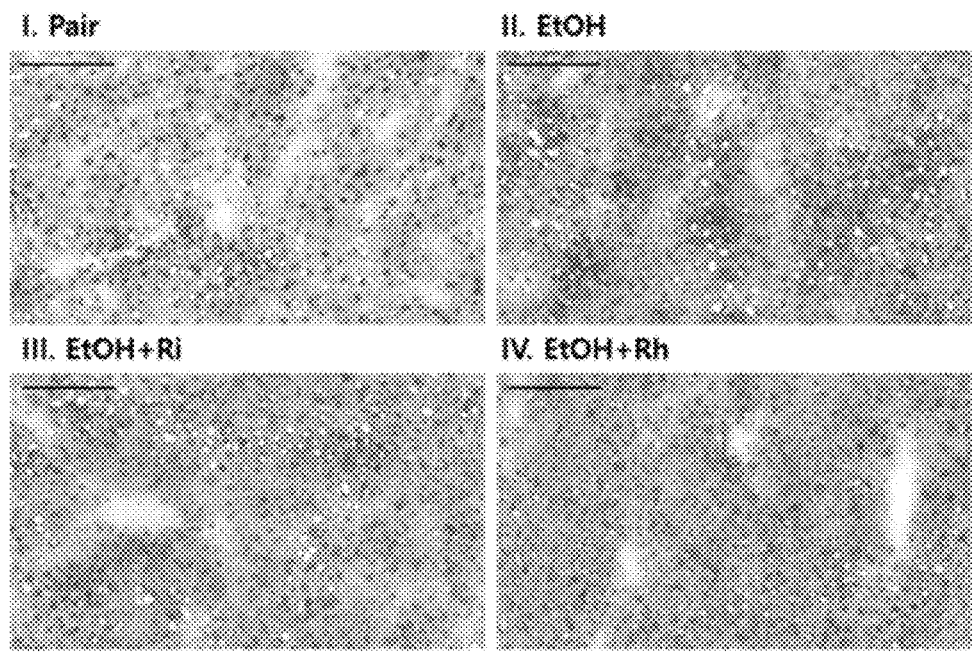

[FIG. 13b]
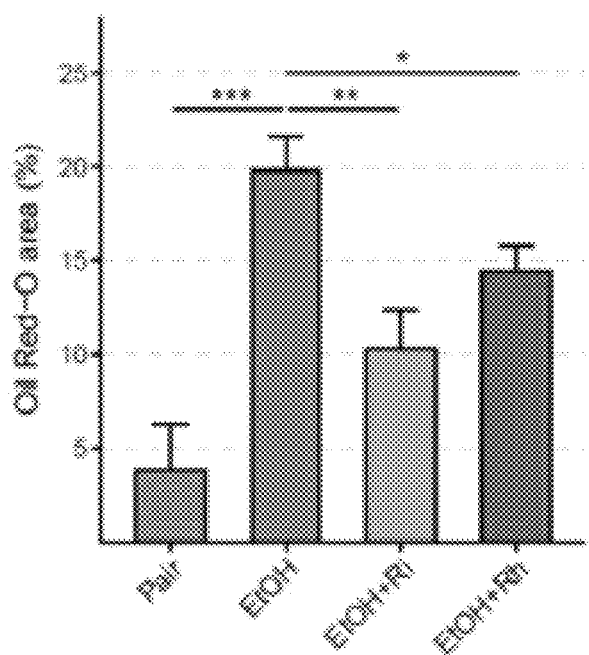

[FIG. 14]
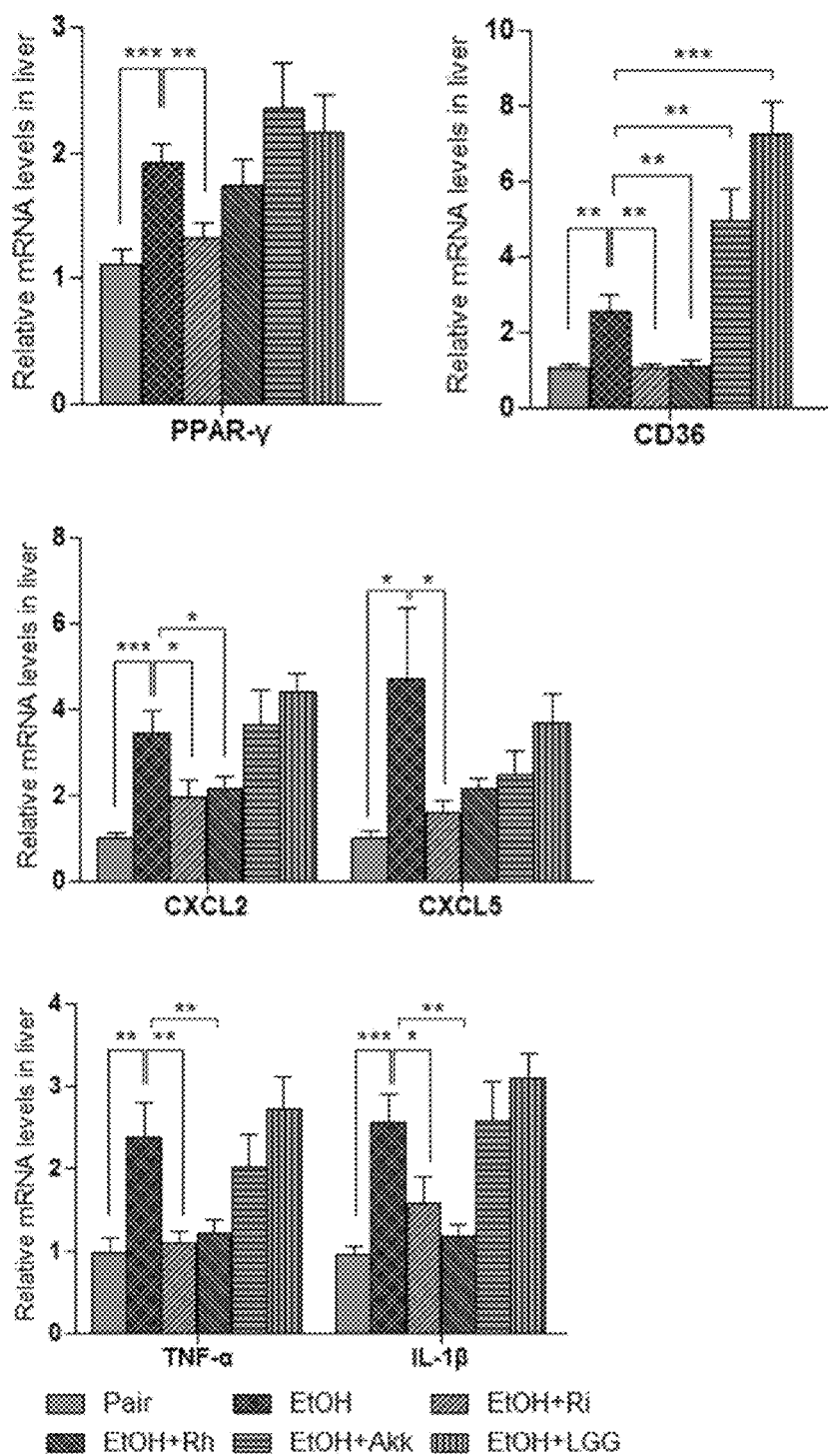

[FIG. 15a]
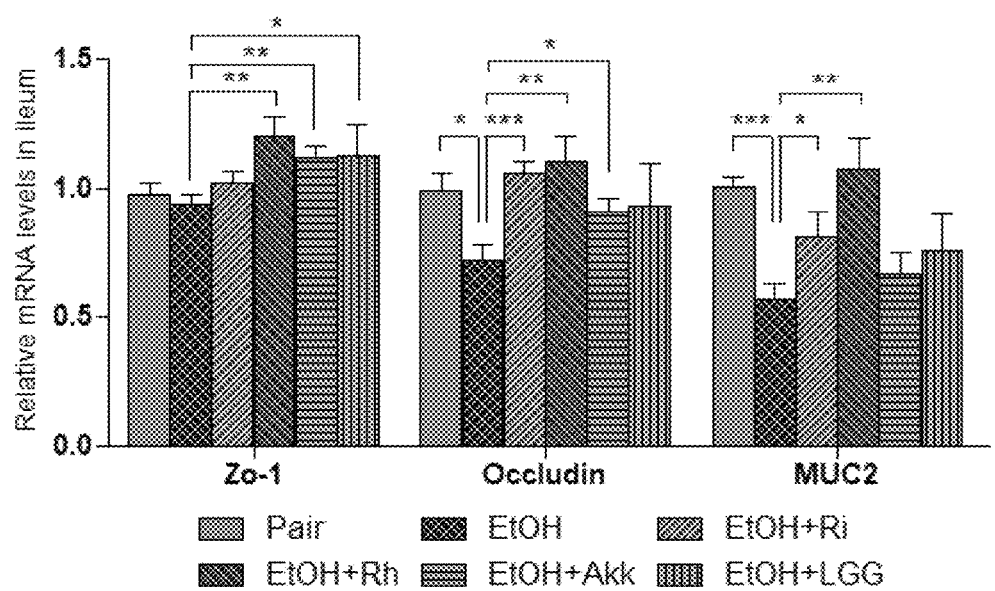

[FIG. 15b]
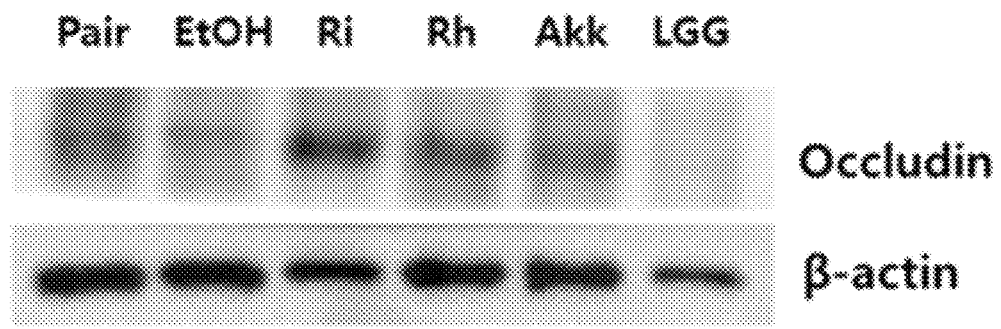

[FIG. 15c]
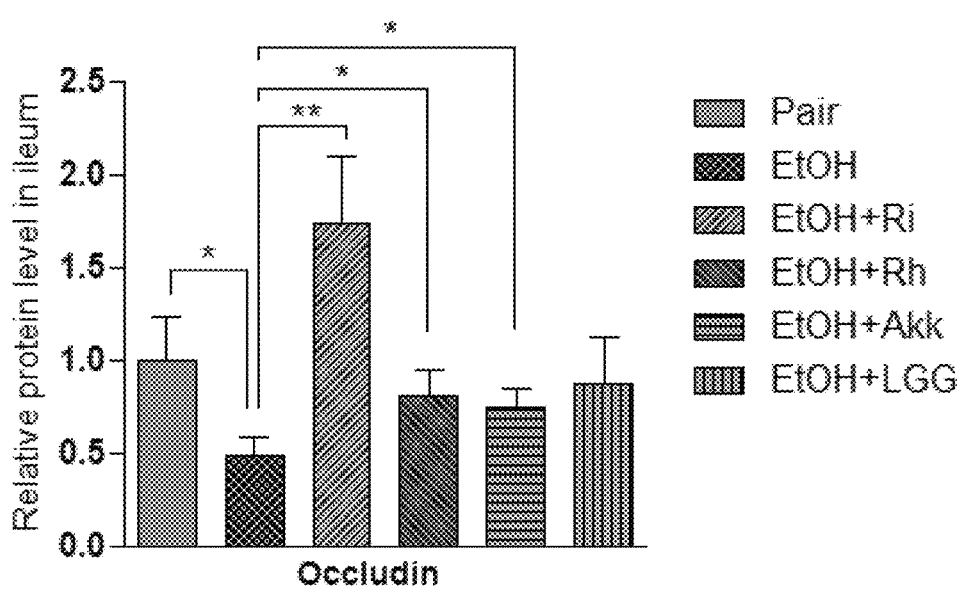

[FIG. 16a]
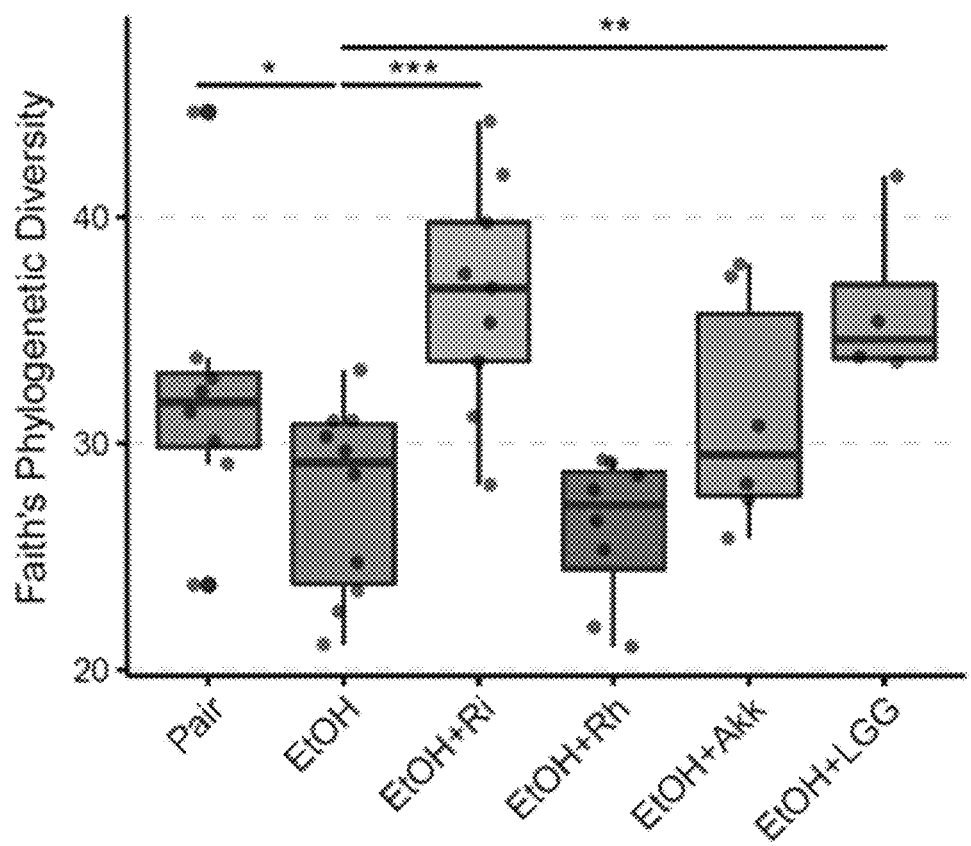

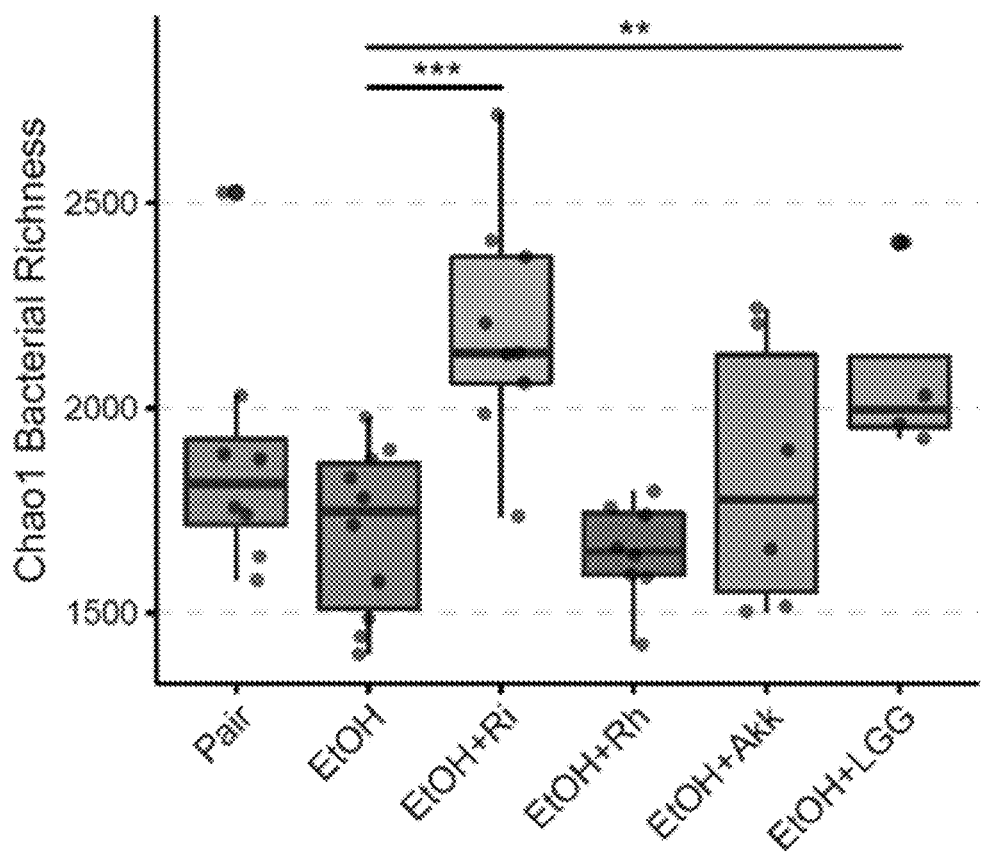
[FIG. 16b]

[FIG. 16c]
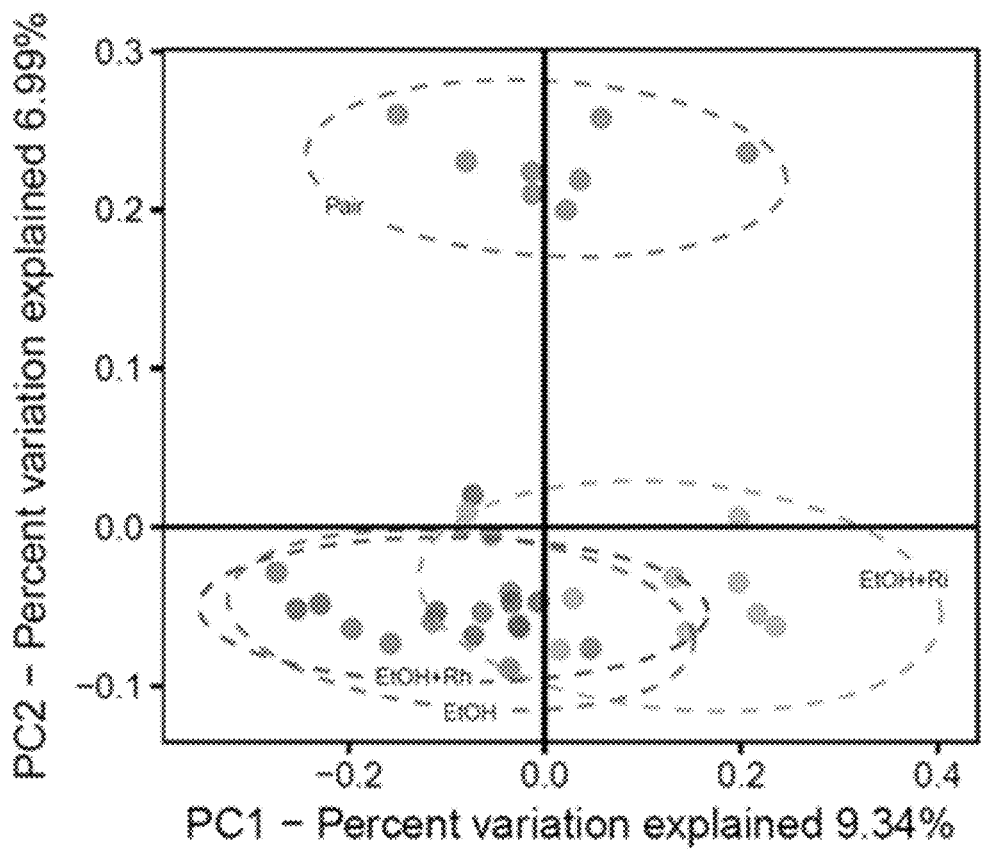

[FIG. 16d]
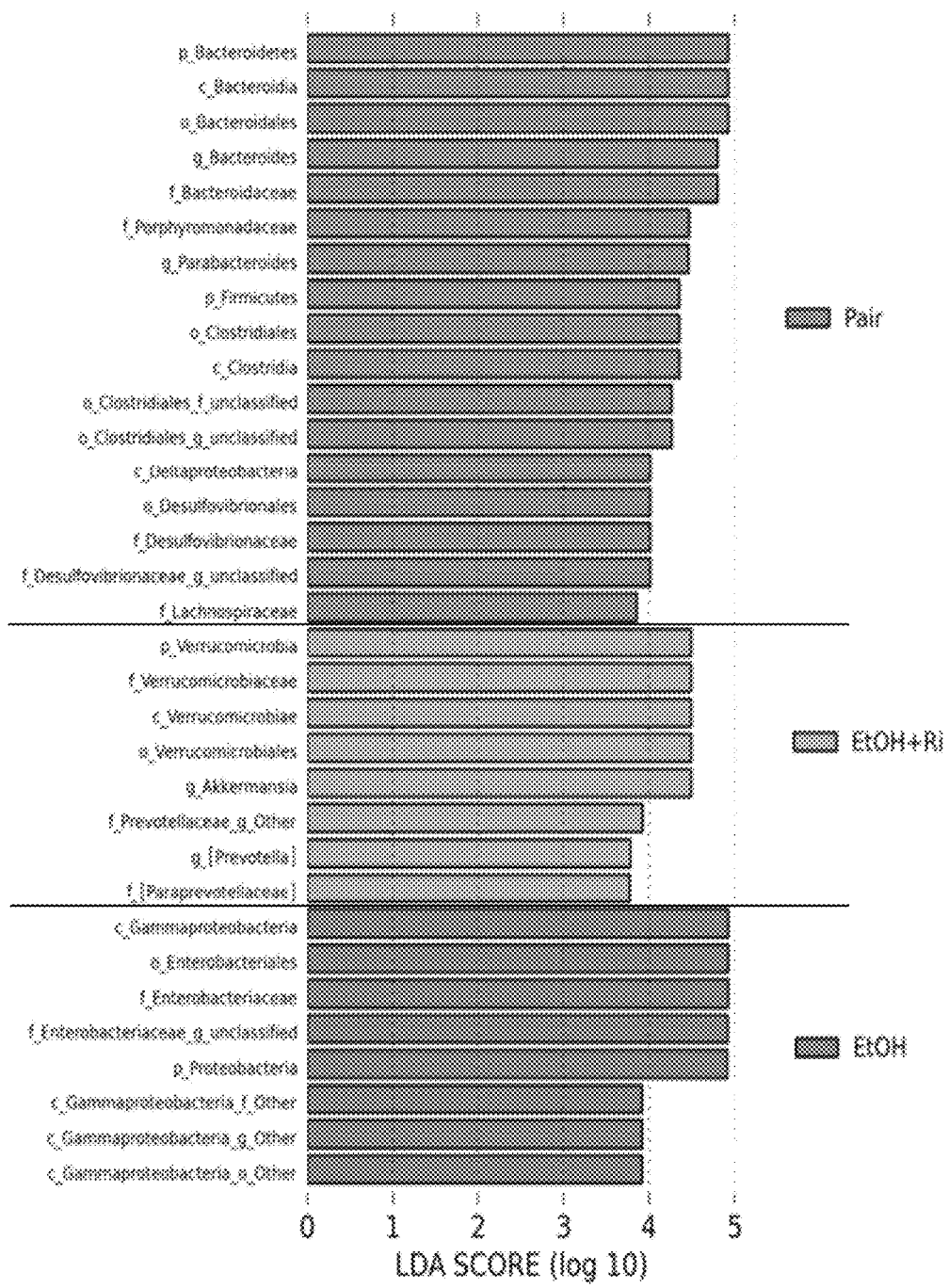

[FIG. 17]
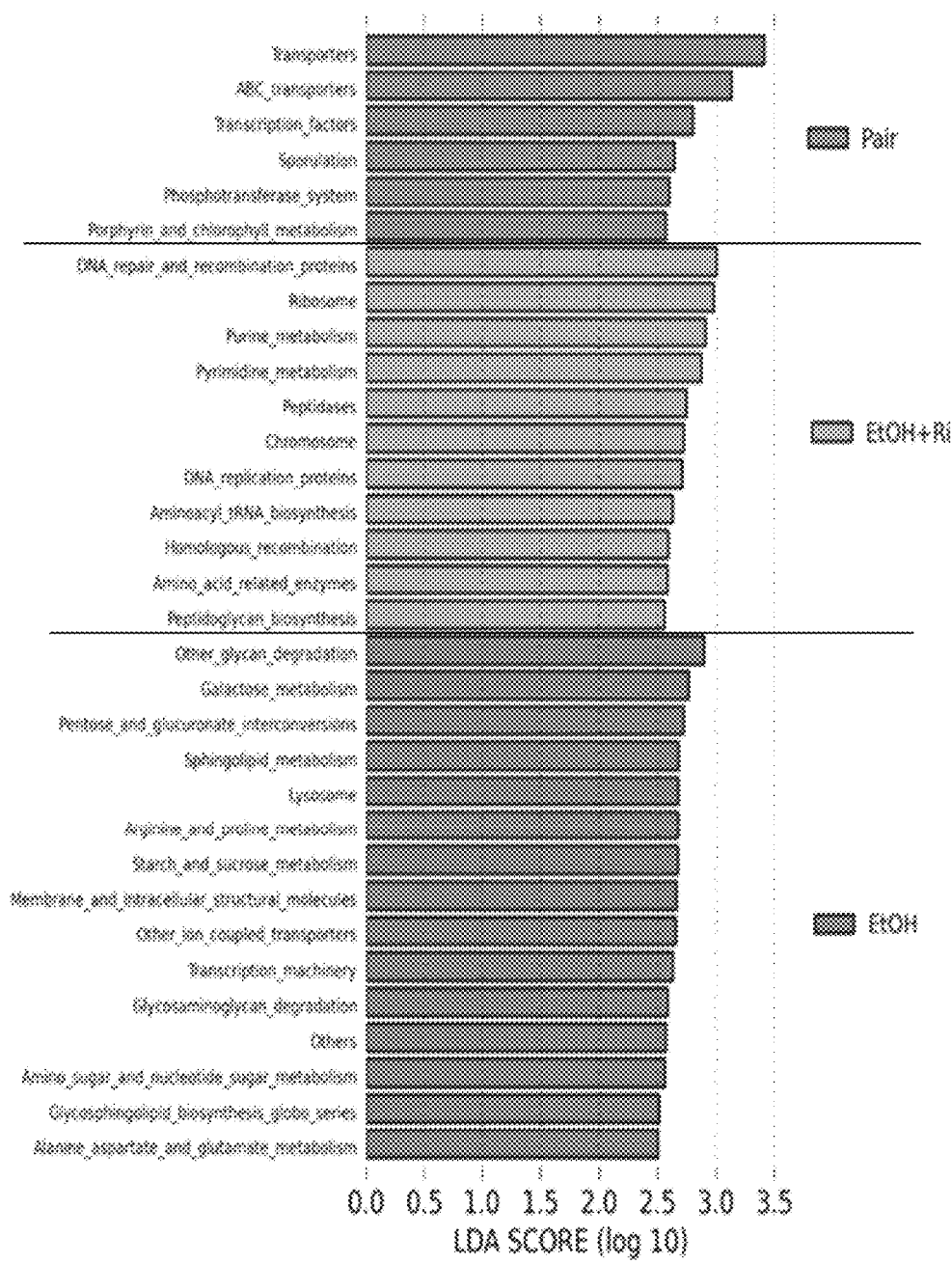

COMPOSITION FOR DIAGNOSIS AND TREATMENT OF ALCOHOLIC LIVER DISEASE, USING CHANGE IN SHORT-CHAIN FATTY ACID PRODUCING GUT BACTERIAL COMMUNITY

TECHNICAL FIELD

The present invention relates to a composition for diagnosis of alcoholic fatty liver disease comprising a microorganism of genus *Roseburia* having efficacy of improving alcoholic fatty liver disease symptoms, and an agent capable of detecting the strain, and a kit for predicting or diagnosing risk of alcoholic fatty liver disease using gut microbiota comprising the strain.

BACKGROUND ART

A cause of alcoholic liver disease (ALD) is alcohol, which is easily absorbed in the gastrointestinal tract, and 2~10% of which is removed by kidneys and lungs, and the remainder is mainly oxidized in liver. Chronic drinking is known to induce alcoholic fatty liver disease by causing fat metabolism imbalance of hepatocytes through various pathways.

Conventionally, the alcoholic liver damage mechanism has been known that about 70% of alcohol consumed is converted to acetaldehyde by alcohol dehydrogenases (ADH) and the remaining 30% is converted to acetaldehyde by cytochrome P450 2E1, but recent studies suggest that enterobacteria and lipopolysaccharide (LPS) which is one of endotoxins, which are significantly increased in alcoholic hepatitis patients, are important causes of alcoholic liver damage.

The composition proportion of gut microbiota is closely related to the immune status of the human body. When tight junctions between gut epithelial cells are inhibited and a leaky gut phenomenon occurs by chronic drinking, the LPS of gut gram-negative bacteria moves a lot through portal vein, and induces severe liver damage due to induction of the activity of Kupffer cells in liver and production of inflammatory cytokines.

Bacterial cluster analysis using a next-generation sequence analysis method has enabled analysis of microbiota including non-culture, and studies are underway to determine the association between microbial genome diversity and diseases.

Gut microbiota may be involved in disease symptoms of secondary organs such as liver, brain and kidneys in addition to intestinal systemic immunity, and it has been found that not only the composition proportion of gut microbiota but also acquisition of specific strains are very important for the immune system.

Therefore, it is necessary to identify intestinal microorganisms having an effect of improving alcoholic fatty liver disease symptoms, to develop a technology for diagnosing alcoholic fatty liver disease using the same.

DISCLOSURE

Technical Problem

An object of the present invention is to provide a *Roseburia* sp. strain with activity of improving alcoholic fatty liver disease.

An object of the present invention is to provide a composition for diagnosis of alcoholic fatty liver disease comprising an agent capable of detecting a gut *Roseburia* sp. strain.

An object of the present invention is to provide a method for providing information relating to diagnosis of alcoholic fatty liver disease comprising the first step of measuring the amount of *Roseburia* sp. strain having activity of alleviating alcoholic fatty liver disease symptoms which is present in gut of a subject;

the second step of measuring the amount of *Roseburia* sp. strain having activity of alleviating alcoholic fatty liver disease symptoms which is present in gut of the control group treated with alcohol intake; and the third step of comparing the amounts of *Roseburia* sp. strain measured in the first step and the second step.

Technical Solution

The present invention relates to gut microbiota analysis using a next generation sequence analysis method and development of a microbiome biomarker being changed by the amount of intake alcohol by using it, and specifically, a *Roseburia intestinalis* corresponding to the microbiome biomarker has been isolated and an effect of improving symptoms of alcoholic fatty liver disease has been confirmed through a mouse experiment, thereby completing the present invention. Specifically, the present inventors have found the *Roseburia intestinalis* SNUG30017 strain isolated from healthy Korean, have confirmed an effect of improving alcoholic fatty liver disease symptoms, and have completed the present invention.

As one aspect, the present invention relates to a *Roseburia* sp. strain having activity of preventing or improving alcoholic fatty liver disease.

Another embodiment of the present invention relates to a pharmaceutical composition for preventing or treating alcoholic fatty liver disease, comprising one or more kinds selected from the group consisting of a microbial cell of the *Roseburia* sp. strain according to the present invention, flagella extract of the strain, culture of the strain, and concentrate and dried product of the culture.

Other embodiment of the present invention relates to a food composition for preventing or improving alcoholic fatty liver disease, comprising one or more kinds selected from the group consisting of a microbial cell of the *Roseburia* sp. strain according to the present invention, flagella extract of the strain, culture of the strain, and concentrate and dried product of the culture.

Other embodiment of the present invention relates to a probiotics preparation for preventing or improving alcoholic fatty liver disease, comprising one or more kinds selected from the group consisting of a microbial cell of the *Roseburia* sp. strain according to the present invention, flagella extract of the strain, culture of the strain, and concentrate and dried product of the culture.

The *Roseburia* sp. strain may cause an increase in diversity of gut microbiota, or an increase in functionality of gut microbiota associated with metabolism.

Other embodiment of the present invention relates to a composition for diagnosing alcoholic fatty liver disease comprising an agent for quantifying the *Roseburia* sp. strain according to the present invention, present in gut of a subject.

The composition may comprise an agent for quantifying the concentration of butyric acid and propionic acid which are fatty acid metabolites.

Other embodiment of the present invention relates to a method for providing information relating to diagnosis of alcoholic fatty liver disease comprising the first step of measuring the amount of *Roseburia* sp. strain having activity of alleviating alcoholic fatty liver disease symptoms which is present in gut of a subject; the second step of measuring the amount of *Roseburia* sp. strain having activity of alleviating alcoholic fatty liver disease symptoms which is present in gut of the control group treated with alcohol intake; and the third step of comparing the amounts of *Roseburia* sp. strain measured in the first step and the second step.

Hereinafter, the present invention will be described in more detail.

The *Roseburia* sp. strain having activity of improving alcoholic fatty liver disease according to the present invention shows correlation for example, in the normal group with little alcohol intake as the result of gut microbiota analysis after alcohol intake, and the *Roseburia* sp. strain showing the correlation is selected as the *Roseburia* sp. strain having activity of improving alcoholic fatty liver disease according to the present invention. The *Roseburia* sp. strain of the present invention may be derived from gut microbiota.

The *Roseburia* sp. strain may show activity of improving alcoholic fatty liver disease by strengthening tight junctions between intestinal epithelial cells. Specifically, it has been confirmed that when the *Roseburia* sp. strain is added, the epithelial resistance of the epithelia cell membrane is increased, and binding between intestinal epithelial cells is strengthened (Example 7).

The *Roseburia* sp. strain may be one or more kinds selected from the group consisting of *Roseburia intestinalis*, and *Roseburia hominis*.

The *Roseburia* sp. strain may be *Roseburia intestinalis*.

The *Roseburia* sp. strain may be *Roseburia intestinalis* SNUG30017.

The *Roseburia* sp. strain may be *Roseburia hominis* DSM 16839.

The *Roseburia* sp. strain according to the present invention may be a strain having at least one characteristic as follows.

(1) Strengthening tight junctions between epithelial cells, increasing epithelial resistance of epithelial cell membrane, increasing of expression of Zo-1 and Occludin genes, or increasing of expression of MUC2 gene, (2) reducing the concentration of causative materials of alcoholic fatty liver, for example, blood lipopolysaccharide (LPS), (3) improving of liver damage, reduction of blood ALT concentration, reduction of blood AST concentration, reduction of triglycerides of liver, reduction of blood FITC fluorescence expression during FITC administration by in vivo barrier permeability experiment, or reduction of the amount of fat of liver as the result of Oil Red O staining, (4) reduction of expression of fatty liver-causing genes, or reduction of expression of PPAR-γ and CD36 genes, (5) improvement or treatment of liver damage symptoms, or reduction of expression of CXCL2 and CXCL5 genes, (6) reduction of inflammatory reactions in liver, or reduction of expression of TNF-α and IL-1β genes, (7) gut microbiota recovery and diversity increase, (8) DNA repair and metabolism-related gut microbiota functionality increase.

The characteristic of strengthening tight junctions between epithelial cells of the *Roseburia* sp. strain according to one embodiment of the present invention means maintaining or increasing the function of tight junctions, and specifically, it may be increasing tight junction activity, or increasing mRNA expression of tight junction protein, for example, membrane protein, occludin. The *Roseburia* sp. strain according to one embodiment of the present invention increases tight junction protein expression in the human derived large intestine cell line, Caco-2 cell line to improve the tight junction characteristic between intestinal cells.

For example, in 24 hours after administering the strain into Caco-2 cell, the increase rate (%) of the transepithelial Electrical Resistance (TEER) is shown to be 1 time or more, 1.2 times or more, 1.4 times or more, 1.6 times or more, 1.8 times or more, or 2 times or more, compared to the control group (FIG. 8a), and there is an effect of strengthening binding between epithelial cells, and alcoholic fatty liver disease symptoms can be alleviated.

TEER is a quantitative technology widely accepted to measure integrity of tight junction dynamics in a cell culture model of endothelial and epithelial monolayers. The TEER values are strong indicators showing integrity of cell barrier before estimating delivery of drugs or chemical substances. TEER measurements can be performed in real time without cell damage, and generally, it is based on Ohmic resistance measurement or impedance measurement in a wide frequency spectrum. The barrier model widely characterized by utilizing TEER includes a gastrointestinal (GI) vascular model, and it may be utilized as indexes of electrical resistance/integrity of intestinal interepithelial gap of the gastrointestinal cell layer.

For example, when the *Roseburia* sp. strain is administered, Zo-1 expression may be 100% or more, 105% or more, 110% or more, or 120% or more, compared to the control group (FIG. 15a).

For example, when the *Roseburia* sp. strain according to one embodiment of the present invention, the Occludin expression may be 100% or more, 105% or more, 110% or more, 115% or more, 120% or more, 125% or more, 130% or more, 135% or more, or 140% or more, compared to the control group (FIG. 15a).

For example, when the *Roseburia* sp. strain according to one embodiment of the present invention, the MUC2 expression may be 100% or more, 105% or more, 110% or more, 115% or more, 120% or more, 125% or more, 130% or more, 135% or more, or 140% or more, compared to the control group (FIG. 15a).

The effect of reducing causative materials of alcoholic fatty liver disease of the *Roseburia* sp. strain according to one embodiment of the present invention may reduce the blood concentration of lipopolysaccharides (LPS) which is a causative material of alcoholic fatty liver disease or alcoholic hepatitis, to improve alcoholic fatty liver. For example, when the *Roseburia* sp. strain is administered with alcohol to C57BL/6J mouse, the blood LPS concentration may be 90% or less, 85% or less, 80% or less, 75% or less, 70% or less, 65% or less, or 62% or less, compared to the control group in which only ethanol is administered (FIG. 11).

The effect of improvement or treatment of liver damage of the *Roseburia* sp. strain according to one embodiment of the present invention may improve alcoholic fatty liver, thereby reducing blood ALT concentration, blood AST concentration, triglycerides of liver, blood FITC fluorescence expression during FITC administration by an in vivo barrier permeability experiment, and/or the amount of fat of liver as the result of Oil Red O staining, which are indexes showing the degree of liver damage, in the *Roseburia* sp. strain-treated group, compared to the control group untreated with the *Roseburia* sp. strain.

For example, when the *Roseburia* sp. strain according to one embodiment of the present invention is administered, the blood ALT concentration may be 100% or less, 95% or less, 90% or less, 85% or less, 80% or less, 75% or less, 70% or less, 65% or less, 60% or less, or 50% or less, compared to the control group.

For example, when the *Roseburia* sp. strain according to one embodiment of the present invention is administered, the blood AST concentration may be 100% or less, 95% or less, 90% or less, 85% or less, 80% or less, 75% or less, 70% or less, 65% or less, 60% or less, or 50% or less, compared to the control group.

For example, when the *Roseburia* sp. strain according to one embodiment of the present invention is administered, the liver triglyceride concentration (Liver TG) may be 100% or less, 95% or less, 90% or less, 85% or less, 80% or less, 75% or less, 70% or less, 65% or less, 60% or less, or 50% or less, compared to the control group.

For example, when the *Roseburia* sp. strain according to one embodiment of the present invention is administered, the blood FITC fluorescence expression may be 100% or less, 95% or less, 90% or less, 85% or less, 80% or less, 75% or less, 74% or less, or 73% or less, compared to the control group.

For example, when the *Roseburia* sp. strain according to one embodiment of the present invention is administered, the amount of fat as the result of Oil Red O staining may be 100% or less, 95% or less, 90% or less, 85% or less, 80% or less, 75% or less, 70% or less, 65% or less, 60% or less, 55% or less, or 50% or less, compared to the control group.

The *Roseburia* sp. strain according to one embodiment of the present invention may improve alcoholic fatty liver, and when the *Roseburia* sp. strain is administered with alcohol, the expression of fatty liver-causing genes is reduced on the *Roseburia* sp. strain-treated group, compared to the control group untreated with the *Roseburia* sp. strain, thereby confirming the effect of improving fatty liver caused by alcohol.

For example, when the *Roseburia* sp. strain according to one embodiment of the present invention is administered, the expression of PPAR-γ which is a gene related to fat metabolism such as triglyceride synthesis and fatty acid transport in liver may be 90% or less, 85% or less, 80% or less, or 75% or less, compared to the control group (FIG. 14).

For example, when the *Roseburia* sp. strain according to one embodiment of the present invention is administered, the expression of CD36 which is a gene related to fat metabolism such as triglyceride synthesis and fatty acid transport in liver may be 90% or less, 85% or less, 80% or less, 75% or less, 70% or less, 65% or less, 60% or less, 50% or less, 45% or less, 40% or less, 35% or less, 30% or less, or 25% or less, compared to the control group.

The *Roseburia* sp. strain according to one embodiment of the present invention can improve an increase of inflammatory reactions in liver occurred by alcohol, and when the *Roseburia* sp. strain is administered with alcohol, the expression of an inflammatory cytokine or chemokine gene is reduced on the *Roseburia* sp. strain-treated group, compared to the control group untreated with the *Roseburia* sp. strain, thereby confirming the effect of improvement of fatty liver occurred by alcohol.

For example, when the *Roseburia* sp. strain according to one embodiment of the present invention is administered, the expression of CXCL2 and/or CXCL5 genes which are chemokines activating neutrophil recruitment as one of inflammatory cytokines, may be 90% or less, 85% or less, 80% or less, 75% or less, 70% or less, 65% or less, 60% or less, 50% or less, 45% or less, 40% or less, 35% or less, 30% or less, or 25% or less, compared to the control group.

For example, when the *Roseburia* sp. strain according to one embodiment of the present invention is administered, the expression of TNF-α and/or IL-1β genes known as inflammatory cytokines, may be 90% or less, 85% or less, 80% or less, 75% or less, 70% or less, 65% or less, 60% or less, 50% or less, 45% or less, 40% or less, 35% or less, 30% or less, or 25% or less, compared to the control group.

The characteristic of strengthening tight junctions between epithelial cells of the *Roseburia* sp. strain according to one embodiment of the present invention may be due to flagella of the *Roseburia* sp. strain. Specifically, in Example 8, as the result of measuring the transepithelial electrical resistance (TEER) of gut epithelial membrane and FITC permeability, after treating the *Roseburia* sp. strain, culture of the *Roseburia* sp. strain and flagella of the *Roseburia* sp. strain, respectively, it has been confirmed that when the flagella of the *Roseburia* sp. strain are added, the transepithelial electrical resistance is significantly increased, and there is an effect of strengthening binding between gut epithelial cells in the *Roseburia* sp. strain-derived flagella, and alcoholic fatty liver disease can be improved.

The pharmaceutical composition of the present invention may be used by formulating into oral formulations such as powder, granules, tablets, capsules, ointment, suspension, emulsion, syrup, aerosol, and the like, or parenteral formulations such as percutaneous agents, suppositories, and sterile injection solution, or the like, according to common methods, respectively.

When the pharmaceutical composition according to the present invention is provided as a parenteral formulation, as one example, it may be a local administering agent such as liquids, gels, cleaning compositions, tablets, suppositories, cream, ointment, dressing solution, spray, other liniments, and the like, or a liquid formulation such as solution, suspension, emulsion, and the like, and it may include a skin external application such as sterile aqueous solution, non-aqueous solvent, suspension, emulsion, freeze-drying agents, suppositories, cream, ointment, jelly, foam, or detergent, preferably, liquids, gels, cleaning compositions, or the like. The formulation may be prepared by adding a solubilizer, emulsifier, buffer for pH regulation, or the like to sterile water, as one example.

As the non-aqueous solvent or suspension, propylene glycol, polyethylene glycol, plant oil such as olive oil, injectable ester such as ethyl oleate, or the like may be used.

The pharmaceutical composition of the present invention may further contain a pharmaceutically suitable and physiologically acceptable adjuvant such as a carrier, excipient and diluent, and the like.

The carrier, excipient and diluent to be comprised in the pharmaceutical composition of the present invention may be lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxy benzoate, propyl hydroxy benzoate, talc, magnesium stearate, and mineral oil. When formulating, a diluent or excipient such as a commonly used filler, extender, binding agent, wetting agent, disintegrating agent, surfactant, or the like may be used.

The pharmaceutical composition according to the present invention may be administered into mammals including humans through various routes. The administration method may be all the commonly used methods, and for example, it may be administered through oral, dermal, intravenous, intramuscular, subcutaneous routes, and the like, and preferably, it may be orally administered.

In a specific embodiment of applying the pharmaceutical composition of the present invention into a human, the pharmaceutical composition of the present invention may be administered alone, but generally, it may be administered by mixing with a pharmaceutical carrier selected in consideration of the administration method and standard pharmaceutical practice.

For example, the composition containing the *Roseburia* sp. strain of the present invention may be administered orally, parenterally, or sublingually, as a tablet form containing starch or lactose, or a capsule form alone or containing an excipient, or an elixir or suspension form containing chemicals flavoring or coloring.

The dosage of the pharmaceutical composition of the present invention may differ according to the age, body weight, gender, administration form, health condition, and disease degree of patients, and it may be administered as divided once to several times a day at regular intervals, depending on the decision of a doctor or pharmacist. For example, the daily dose may be 0.1 to 500 mg/kg, preferably, 0.5 to 300 mg/kg, based on the content of active ingredients. The dose is illustrative of the average case, and may be high or low depending on individual differences.

In addition, when the daily dose of the pharmaceutical composition of the present invention is less than the dosage, a significant effect cannot be obtained, and when it is over it, it is non-economical and also it is over the range of the average dose, and therefore undesirable side-effects may be caused, and thus the above range is preferable.

For the food composition for prevention or improvement of alcoholic fatty liver disease according to other embodiment of the present invention, food means a natural product or processed good containing one or more of nutrients, and preferably, means that it can be directly eaten after a certain degree of processing, and it is intended to include all foods, food additives, health functional foods, beverages and beverage additives in a conventional meaning. In the present invention, beverage is a generic term for drinking to quench thirst or to enjoy a taste and is intended to include functional beverages.

The *Roseburia* sp. strain according to one embodiment of the present invention may be contained in various edible products such as dairy products, yogurt, curd, cheese (e.g. quark, cream, processed, soft and hard), fermented oil, powdered milk, milk-based fermented products, ice cream, fermented cereal based products, milk based powder, beverages, dressing and pet feed. The term "food" herein is the broadest meaning, including all types of products, in all provided forms, which can be ingested by animals, except pharmaceutical products and veterinary products.

For the beverage, there is no particular limitation in liquid components, except for containing the *Roseburia* sp. strain as an essential component, and as common beverages, it may contain various flavors or natural carbohydrate, or the like as an additional component.

The example of the aforementioned natural carbohydrate is a common sugar such as monosaccharides, for example, glucose, fructose, and the like, disaccharides, for example, maltose, sucrose, and the like, and polysaccharides, for example, dextrin, cyclodextrin, and the like, and a sugar-alcohol such as xylitol, sorbitol, erythritol, and the like. As a flavor in addition to the above, natural flavors (thaumatin, stevia extract (for example, rebaudioside A, glycyrrhizin, and the like)) and synthetic flavors (saccharin, aspartame, and the like) may be advantageously used. The ratio of natural carbohydrate is generally about 1 to 20 g, preferably, about 5 to 12 g per 100 ml of the food composition of the present invention.

The food composition of the present invention may contain various nutritional supplements, vitamins, minerals (electrolytes), flavors such as synthetic flavors and natural flavors, and the like, coloring agents and fillers (cheese, chocolate, and the like), pectic acid and its salts, alginate and its salt, organic acids, protective colloidal thickeners, pH adjusting agents, stabilizers, preservatives, glycerin, alcohol, carbonizing agents used in carbonated drinks, and the like.

In addition, the food composition of the present invention may contain flesh for preparation of natural fruit juice and fruit juice beverages and vegetable beverages. These components may be used independently or in combination.

When the composition according to the present invention is used as dietary supplements, it may be administered as it is, or be mixed with suitable drinkable liquids such as water, yogurt, milk or fruit juice, or the like, or be mixed with solid or liquid food. In this aspect, the dietary supplements may be tablets, pills, capsules, granules, powder, suspension, sachet, pastille, sweet, bar, syrup and in corresponding dose forms, generally in a unit dose form. Preferably, the composition of the present invention may be administered in a form of tablets, capsules or powder, prepared by a common preparation process of a pharmaceutical product.

The content of the *Roseburia* sp. strain as an active ingredient contained in the food composition according to one embodiment of the present invention may be appropriately adjusted according to food forms, desired use, and the like without particular limitation, and for example, one or more kinds selected from the group consisting of the microbial cell of the *Roseburia* sp. strain, culture of the *Roseburia* sp. strain, lysate of the strain and extract of the strain, as an active ingredient of the total food weight may be added in an amount of 0.00001% by weight to 100% by weight, 0.001% by weight to 99.9% by weight, 0.1% by weight to 99% by weight, more preferably, 1% by weight to 50% by weight, 0.01 to 15% by weight. For example, it may be added at a ratio of 0.02 to 10 g, preferably, 0.3 to 1 g, based on the food composition of 100 ml.

The *Roseburia* sp. strain according to one embodiment of the present invention, in particular, has an advantage of being available as probiotics, and accordingly, a probiotics composition comprising the *Roseburia* sp. strain according to the present invention may be provided. The *Roseburia* sp. strain according to the present invention may be used as a useful probiotics preparation, by having a characteristic of preventing or improving alcoholic fatty liver.

Probiotic bacteria should satisfy several requirements related to toxicity deficiency, viability, adherence and useful effects. These probiotic characteristics are strain-dependent even in the same species of bacteria. Therefore, it is important to develop a strain showing an excellent performance to all the probiotic requirements, and it has been demonstrated that the strain has excellent probiotic characteristics. In addition, a preferable condition of a strain to be used in the probiotics composition may include low activity loss in stomach and resistance to various antibiotics in the intestine.

Probiotics is defined as "living microorganisms providing health advantages beyond essential basic nutrition, when consumed in a certain number (Araya M. et al., 2002; Guarner F. et al., 1998). A number of kinds of lactic acid bacteria and *Bifidobacterium* species are included to probiotics, and this means that these strains have been demonstrated to promote specific health effects. Probiotic bacteria should satisfy several requirements related to toxicity deficiency, viability, adherence and useful effects. In addition, it has been reported that the gut immunity improving effect should be accompanied by maintenance of function of tight junctions between intestinal cells and reduction of inflammatory cytokines, increase of anti-inflammatory cytokines, maintenance of balance of gut microbiota and the like. Therefore, it is important to develop strains having an excellent performance for all the probiotics requirements.

Thus, a preferable condition of a strain to be used in the probiotics composition may include low activity loss in stomach and resistance to various antibiotics in the intestine.

The term used herein, "marker for diagnosis or diagnosis marker" is a material to be a standard that distinguishes between states of alcoholic fatty liver disease and those not, and includes various organic biomolecules showing an increase or decrease in a sample of a patient with alcoholic fatty liver disease compared to a normal sample, and the like. For the purpose of the present invention, the composition for diagnosis according to one embodiment of the present invention refers to the *Roseburia* sp. strain expressed at a specifically high level in an alcoholic fatty liver disease patient, and refers to a *Ruminococcus* sp. strain, *Blautia* sp. strain, and/or *Clostridium* sp. strain microorganism or cluster, which has positive correlation with the corresponding strain.

Preferably, the detectable agent means a material to be used for detecting presence of *Roseburia* sp. strain, *Ruminococcus* sp. strain, *Blautia* sp. strain, and/or *Clostridium* sp. strain, that are diagnosis markers of alcoholic fatty liver, in a sample. For example, it may be one or more selected from the group consisting of a primer, probe, antisense oligonucleotide, aptamer and antibody, which can specifically detect organic biomolecules such as protein, nucleic acid, lipid, glycolipid, glycoprotein or sugar (monosaccharide, disaccharide, oligosaccharide, and the like), and the like, specifically present in the *Roseburia* sp. strain, *Ruminococcus* sp. strain, *Blautia* sp. strain, and/or *Clostridium* sp. strain.

Herein, a microorganism detecting agent may be an antibody, and the corresponding microorganism can be detected using an immunological method based on an antigen-antibody reaction. The analysis method for this includes western blot, ELISA (enzyme linked immunosorbent assay), radioimmunodiffusion, Ouchterlony immunodiffusion, rocket immunoelectrophoresis, immunohistostaining, immunoprecipitation assay, Complement Fixation Assay, FACS (Fluorescence activated cell sorter), protein chip and the like, but not limited thereto.

The term used herein, "risk prediction" refers to determination of whether a test subject is likely to develop alcoholic fatty liver disease or related disease, and it may be clinically used to delay the onset or stop the onset through special and appropriate management of the test subject with high risk of development of alcoholic fatty liver disease or occurrence of related disease, or to determine treatment by selecting the most suitable treatment methods. In addition, "diagnosis" means confirming presence or characteristics of the pathological condition, and for the purpose of the present invention, diagnosis may mean confirming development of alcoholic fatty liver disease or occurrence of related disease.

According to one embodiment of the present invention, a composition comprising an agent capable of detecting the *Roseburia* sp. strain may detect alcoholic fatty liver disease or alcoholic fatty liver-related disease with significant sensitivity, comprising all the strains with high detection specificity.

As other one embodiment of the present invention, the composition comprising the agent for detecting a microorganism of the present invention may be provided as implemented as a kit form for risk prediction or diagnosis of alcoholic fatty liver disease or alcoholic fatty liver-related disease. The kit of the present invention may comprise a detection agent such as a primer, probe, antisense oligonucleotide, aptamer and/or antibody for detecting the corresponding microorganisms, and in addition, may comprise one or more kinds of other component compositions, liquids or devices suitable for the analysis method.

As one specific example, the kit comprising a primer specific to the corresponding microorganism in the present invention may be a kit comprising essential elements for performing amplification reaction such as polymerase chain reaction (PCR) and the like. For example, the kit for PCR may comprise a test tube or other appropriate container, reaction butter, deoxynucleotides (dNTPs), enzyme such as Taq-polymerase reverse transcriptase, DNase, RNAse inhibitors, DEPC-water, sterile water, and the like.

The kit may comprise a collecting apparatus for collecting blood or intestinal fluid for collection of a sample, and the collecting apparatus may further comprise one or more kinds of collecting apparatuses selected from the group consisting of a brush, absorptive pad, cotton swab, spuit, swab, syringe and amniotic fluid collector, but any one capable of collecting the biological sample is not limited.

In addition, the kit may further comprise instructions requiring collecting a sample of a test subject for risk prediction or diagnosis of alcoholic fatty liver disease or alcoholic fatty liver-related disease.

As other embodiment of the present invention, the present invention relates to a method for detecting one or more of microorganisms selected from the group consisting of the *Roseburia* sp. strain, *Ruminococcus* sp. strain, *Blautia* sp. strain, and/or *Clostridium* sp. strain, to provide information needed for risk prediction or diagnosis of alcoholic fatty liver disease or alcoholic fatty liver-related disease using the *Roseburia* sp. strain.

The matters related to the composition for risk prediction or diagnosis of alcoholic fatty liver disease or alcoholic fatty liver-related disease can be equally applied to the method for detecting the microorganism.

Preferably, the method may be implemented by comprising (a) collecting a sample of a test subject; (b) extracting genome DNA from the sample; reacting a primer specific to the *Roseburia* sp. strain to the extracted genome DNA; and (c) amplifying the reacted products.

In the step (a), "sample of a test subject" is collected from the human body predicted as a patient of alcoholic fatty liver disease or alcoholic fatty liver-related disease, and includes samples such as blood, intestinal fluid, tissue, cell, whole blood, serum, plasma saliva, feces or urine, but for example, it may be blood, intestinal fluid, tissue collected from the intestine of the test subject, and preferably, a feces sample.

In the step (b), extraction of genome DNA from the sample of the test subject may be performed by applying common technologies known to the art, and the primer specific to the *Roseburia* sp. strain is as described above.

In the step (c), the method for amplifying reacted products may be common amplifying technologies known in the art, for example, polymerase chain reaction, SYBR real-time PCR, reverse transcription-polymerase chain reaction, multiplex PCR, touchdown PCR, hot start PCR, nested PCR, booster PCR, real-time PCR, differential display PCR, rapid amplification of cRNA terminus, inverse PCR, vectorette PCR, TAIL-PCR, ligase chain reaction, repair chain reaction, transcription-mediated amplification, self-sustained sequence replication, and selective amplification reaction of a target sequence, but the scope of the present invention is not limited thereto.

In addition, (d) comparing the amount of amplified products in the step (c) with the amplified products of a normal control group sample may be further performed, and when it is determined that the amplified products of the sample of the test subject is significantly increased or decreased, compared to the amplified products of the normal control group sample, the corresponding test subject may be determined to have alcoholic fatty liver disease or alcoholic fatty liver disease.

Preferably, when the amplified products for the microorganism of the *Roseburia* sp. strain of the test subject sample is lower than the normal control group sample, it may be predicted to have a risk of alcoholic fatty liver disease or alcoholic fatty liver disease, or be diagnosed to have alcoholic fatty liver disease or alcoholic fatty liver disease.

Advantageous Effects

The present invention relates to a *Roseburia* sp. strain which can be utilized as a novel biomarker of alcoholic fatty liver disease by correlation analysis of gut microbiota changing according to alcohol intake based on a Korean twin cohort, and using the *Roseburia* sp. strain of the present invention, it is possible to develop or utilize a kit for diagnosis or a composition for treatment of alcoholic fatty liver disease.

BRIEF DESCRIPTION OF THE DRAWINGS

FIG. 1 shows the correlation result of the alcohol intake (g/day) and AUDIT score of the cohort of the present invention, and the age, gender, and C reactive protein (hsCRP) clinical index information by group.

FIG. 2 shows the result of confirming changes in diversity of gut microbiota by classifying the gut microbiota analyzed based on 16S rRNA into AUDIT stages I, II, and III by alcohol intake, according to one embodiment of the present invention.

FIG. 3 is the result of analyzing the association between health factors and gut microbiota by dividing by OTU (Operational Taxonomic Units, 16S based bioinformatics bacterial classification units), according to one embodiment of the present invention.

FIG. 4 is the result of analyzing the association between health factors and gut microbiota by dividing by taxon, according to one embodiment of the present invention.

FIG. 5 is the result of performing network analysis using a cytoscape software, according to one embodiment of the present invention.

FIG. 6 is the result of performing association analysis of short chain fatty acid metabolites after designating age, gender, twins and family relations as random parameters and the alcohol intake group as a correction parameter, according to one embodiment of the present invention.

FIG. 7 is the result of conducting analysis of correlation of metabolites and gut microbiota in 307 samples of which short chain fatty acid metabolites information is secured, according to one embodiment of the present invention.

FIG. 8a is the experimental result of confirming the effect of strengthening tight junctions between intestinal epithelial cells of the *Roseburia intestinalis* SNUG300117 strain according to one embodiment of the present invention.

FIG. 8b is the result of loading protein extract derived from *Roseburia intestinalis* and *Roseburia hominis* strains on SDS-PAGE gel.

FIG. 8c is the result of LTQ-Orbitrap mass spectrometry of protein extract derived from *Roseburia intestinalis* and *Roseburia hominis* strains.

FIG. 8d is the result of observing *Roseburia intestinalis* and *Roseburia hominis* strains with a transmission electron microscope.

FIG. 8e is the result of measuring the epithelial electrical resistance of membrane in 24 hours after adding the *Roseburia* sp. strain, the culture of the *Roseburia* sp. strain, and the flagella of the *Roseburia* sp. strain into Caco-2 cell line.

FIG. 8f is the result of measuring the epithelial electrical resistance of membrane after treating ethanol with 500 mM/well to the Caco-2 cell treated with the *Roseburia* sp. strain, the culture of the *Roseburia* sp. strain, and the flagella of the *Roseburia* sp. strain and culturing for 3 hours.

FIG. 8g is the result of measuring the permeability through fluorescence by FITC permeability after treating FITC-dextran (Fluorescein-dextran) with 1 g/l and culturing for 1 hour.

FIG. 9a is a schematic diagram showing the animal experiment process for confirming the effect of improving alcoholic fatty liver disease of the strain according to the present invention.

FIG. 9b is the result of confirming the effect of improving alcoholic fatty liver disease of the *Roseburia* strain SNUG30017 strain according to one embodiment of the present invention.

FIG. 10 is the result of measuring the weight after extracting liver and appendixes according to one embodiment of the present invention.

FIG. 11 is the result of measuring blood alanine aminotransferase (ALT) and lipopolysaccharides (LPS) composing the cell wall of gram-negative bacteria, according to one embodiment of the present invention.

FIG. 12 is the result of histopathological observation by hematoxylin & eosin (H&E) staining, according to one embodiment of the present invention.

FIG. 13a is the result of performing Oil Red O staining which is a measure of damage to liver tissue, according to one embodiment of the present invention.

FIG. 13b is the result of quantifying red color showing fat using ImageJ program, based on 6 photographs of results of Oil Red O staining on randomly selected regions.

FIG. 14 is the result of confirming the changes of gene expression of liver tissue according to one embodiment of the present invention, and the bars of each graph are the negative control group (Pair), positive control group (EtOH), *Roseburia intestinalis* administration group (EtOH+Ri), *Roseburia hominis* administration group (EtOH+Rh), *Akkermansia muciniphila* administration group (EtOH+Akk), and *Lactobacillus rhamnosus* GG administration group (EtOH+LGG) from the left.

FIG. 15a is the result of confirming the changes of gene expression of intestinal tissue, and the bars of each graph are the negative control group (Pair), positive control group (EtOH), *Roseburia intestinalis* administration group (EtOH+Ri), *Roseburia hominis* administration group (EtOH+Rh), *Akkermansia muciniphila* administration group (EtOH+Akk), and *Lactobacillus rhamnosus* GG administration group (EtOH+LGG) from the left.

FIG. 15b is a western blot photograph of confirming the changes of Occludin and b-actin protein expression of the intestinal tissue.

FIG. 15c is the value of quantifying the protein expression confirmed by western blot in the intestinal tissue and correcting Occludin expression by b-actin, and the bars of each graph are the negative control group (Pair), positive control group (EtOH), *Roseburia intestinalis* administration group (EtOH+Ri), *Roseburia hominis* administration group (EtOH+Rh), *Akkermansia muciniphila* administration group (EtOH+Akk), and *Lactobacillus rhamnosus* GG administration group (EtOH+LGG) from the left.

FIG. 16a is the result of confirming the changes in diversity of gut microbiota analyzed based on 16S rRNA with Faith's Phylogenetic diversity index by group.

FIG. 16b is the result of confirming the changes in diversity of gut microbiota analyzed based on 16S rRNA with Chao1 index by group.

FIG. 16c is the result of conducting analysis of major components of gut microbiota analyzed based on 16S rRNA.

FIG. 16d is the result of conducting univariate analysis (LefSE) for analyzing changes of gut microbiota.

FIG. 17 is the result of conducting gut microbiota KEGG pathways function estimation analysis through PICRUSt.

DETAILED DESCRIPTION OF THE EMBODIMENTS

Hereinafter, the present invention will be described in more detail by the following examples. However, these examples are intended to illustrate the present invention only, but the scope of the present invention is not limited by these examples.

Example 1. Study Objects and Sample Collection

Feces samples were collected from 410 monozygotic and dizygotic twins and their families in Korean twin cohort, and were stored frozen at −80° C. The stored frozen samples were moved to a laboratory and bacteria genomic DNA was extracted using QIAamp FAST DNA stool mini kit (Qiagen). In the present cohort, by utilizing the result of survey of alcohol intake (g/day) and alcohol intake habit which is AUDIT score clinical index, it was analyzed by dividing into Zone I (scores 0-7, normal group), Zone II (scores 8-15), Zone III (scores 16-40, group with high alcohol intake) according to AUDIT score. The result of analyzing the correlation of the alcohol intake (g/day) and AUDIT score of the present cohort, and the age, gender, C reactive protein (hsCRP) clinical index information by group were shown in FIG. 1.

Example 2. Analysis of Gut Microbiota Using 16S rRNA

The DNA extracted in Example 1, was amplified using 515F/806R primers (SEQ ID NOs: 1 and 2) of the following Table 1 targeting V4 region of the bacterial 16S rRNA gene, and sequence data were produced using MiSeq device of Illumina company. The produced bulk sequence was analyzed using QIIME pipeline, and the whole genetic information of gut bacteria was confirmed and the structure of gut microbiota was identified, and then the association with the alcohol intake index was observed.

TABLE 1

| Classification | SEQ ID NO | Nucleic acid sequence (5'->3') |
|---|---|---|
| Forward | 1 | ATGATACGGCGACCACCGAGATCTACACTA TGGTAATTGTGTGCCAGCMGCCGCGGTAA |
| Reverse | 2 | CAAGCAGAAGACGGCATACGAGATAGTCAG TCAGCCGGACTACHVGGGTWTCTAAT |

The result of confirming changes in diversity of gut microbiota analyzed on the basis of 16S rRNA by dividing into AUDIT zone I, II, III according to the alcohol intake was shown in FIG. 2, and it was confirmed that in the group with high alcohol intake, the diversity of gut microbiota was reduced. This suggests that the increase of the alcohol intake may negatively affect the intestine health, due to reduction of diversity of benefit bacteria and predominance of potential harmful bacteria.

Example 3. Analysis of Correlation of Gut Microbiota and Alcohol Intake

Gut bacteria which could specify changes in gut microbiota according to the alcohol intake and thereby intestinal health were investigated through multivariate analysis, using MaAsLin (Multivariate analysis by linear models) software capable of controlling disruption variables by correcting the age, gender, and family history. After designating the age, gender, and family relations with twins as random parameters and designating the alcohol intake group as a correction parameter, using MaAsLin software, the correlation of health factors and gut microbiota were divided by OTU (Operational Taxonomic Units, 16S based bioinformatics bacterial classification unit) and taxon and analyzed, and the results were shown in FIG. 3 and FIG. 4.

As could be confirmed in FIG. 3, it was shown that in the group with high alcohol intake, *Prevotella copri* OUT had the most association, and in the group with low alcohol intake, *Roseburia* OUT had the most association. The result of FIG. 3 showed the same tendency when analyzed by taxon, as could be confirmed in FIG. 4.

Example 4. Analysis of Gut Microbiota Network by Alcohol Intake Group

To investigate the pattern of occurrence of gut microbiota in the group with high alcohol intake and normal group, network analysis was performed using cytoscape software.

The result was shown in FIG. 5, and the result of observing the interrelation of gut microbiota through network analysis, it was found that the gut microbiota was divided into two groups by alcohol intake. Taxa belonging to the same group had the strong positive correlation each other, and had the negative correlation with other groups each other.

Example 5. Analysis of Correlation of Gut Microbiota and Short Chain Fatty Acid Metabolites by Alcohol Intake For the part of Korean twin cohort, 307 feces samples, the gut microbiota-derived metabolite, short chain fatty acid analysis was performed. The same amount of feces samples was dissolved in sterile tertiary distilled water and were oxidized using 95% (v/v) sulfuric acid, and then were centrifuged to collect the supernatant.

To the sample supernatant, for the internal standard, 1% 2-methyl pentanoic acid was added, and then ethyl ether was added. After vortexing it, it was centrifuged to collect the ether layer, and the short chain fatty acid metabolites were analyzed using 6890 GC-FID device of Agilent company. The secured short chain fatty acid metabolite profile was 6 kinds in total, and they were acetic acid, propionic acid, butyric acid, isobutyric acid, valeric acid, and isovaleric acid.

For this profile, using MaAsLin software, after designating the age, gender, and family relations with twins as random parameters and the alcohol intake group as a correction parameter, the association was analyzed.

The experimental result was shown in FIG. 6, and it could be confirmed that the relative presence ratio of butyric acid was reduced as the alcohol intake was high. In addition, it could be confirmed that the ratio of butyric acid to propionic acid was increased as the alcohol intake was high.

Furthermore, for 307 samples of which short chain fatty acid metabolite information was secured, the analysis of correlation of metabolites and gut microbiota was performed. As a result, as could be confirmed in FIG. 7, there was positive correlation of *Roseburia* and butyric acid, and there was positive correlation of *Prevotella* and *Megamonas* with propionic acid.

Through the above result, it could be confirmed that the changes of gut microbiota according to the alcohol intake could induce changes of metabolites, short chain fatty acids, and the gut microbiota and short chain fatty acid metabolites could be used as biomarkers of disease caused by alcohol intake.

Example 6. Isolation and Identification of Korean-Derived *Roseburia* sp. Strain A *Roseburia intestinalis* strain was isolated from the gut microbiota of healthy Korean. Specifically, samples for isolating gut microbiota were provided from health common adults, and the strain was isolated and identified from feces samples (IRB approval number: 1602/001-001).

Feces samples were moved to the present laboratory right after collection, and immediately, were used for strain isolation. After striking samples in YCFAG media comprising 1.5% agar by the direct smear method, they were cultured under the anaerobic condition at 37° C. for 48 hours. Colonies purely isolated after culturing were randomly selected and were cultured in YBHI media, and for strain identification, after extracting genomic DNA of the strain, PCR reaction was performed using 27F/1492R primers (SEQ ID NOs: 3 and 4) of the following Table 2 targeting the 16S rRNA gene.

TABLE 2

| Classification | SEQ ID NO | Sequence (5'->3') |
| --- | --- | --- |
| Forward | 3 | AGAGTTTGATYMTGGCTCAG |
| Reverse | 4 | TACGGYTACCTTGTTACGACT |

After purifying the PCR reacted products using QIAquick PCR purification kit (Qiagen), the sequence analysis was conducted. The result was as the sequence of the following Table 3, and the isolation of the strain was finally completed by multiple comparison by EzBioCloud program of Chunlab using this sequence information.

TABLE 3

| Strain name | Name | Sequence | SEQ ID NO |
| --- | --- | --- | --- |
| Roseburia intestinalis | SNUG30017 | TTATGGCTCAGGATGAACGCTGGCGGCGTGCTTAACACATGC AAGTCGAACGAAGCACTT TATTTGATTTCTTCGGAATGAAGATTTTGTGACTGAGTGGCGG ACGGGTGAGTAACGCGT GGGTAACCTGCCTCATACAGGGGGATAACAGTTGGAAACGAC TGCTAATACCGCATAAGC GCACAGGGTCGCATGACCTGGTGTGAAAAACTCCGGTGGTAT GAGATGGACCCGCGTCTG ATTAGCCAGTTGGTGGGGTAACGGCCTACCAAAGCGACGATC AGTAGCCGACCTGAGAGG GTGACCGGCCACATTGGGACTGAGACACGGCCCAAACTCCTA CGGGAGGCAGCAGTGGGG AATATTGCACAATGGGGGAAACCCTGATGCAGCGACGCCGCG TGAGCGAAGAAGTATTTC GGTATGTAAAGCTCTATCAGCAGGGAAGAAGAAATGACGGTA CCTGACTAAGAAGCACCG GCTAAATACGTGCCAGCAGCCGCGGTAATACGTATGGTGCAA GCGTTATCCGGATTTACT GGGTGTAAAGGGAGCGCAGGCGGTACGGCAAGTCTGATGTGA AAGCCCGGGGCTCAACCC CGGTACTGCATTGGAAACTGTCGGACTAGAGTGTCGGAGGGG TAAGTGGAATTCCTAGTG TAGCGGTGAAATGCGTAGATATTAGGAGGAACACCAGTGGCG AAGGCGGCTTACTGGACG ATTACTGACGCTGAGGCTCGAAAGCGTGGGGAGCAAACAGGA TTAGATACCCTGGTAGTC CACGCCGTAAACGATGAATACTAGGTGTCGGGGAGCATTGCT CTTCGGTGCCGCAGCAAA CGCAATAAGTATTCCACCTGGGGAGTACGTTCGCAAGAATGA AACTCAAAGGAATTGACG GGGACCCGCACAAGCGGTGGAGCATGTGGTTTAATTCGAAGC AACGCGAAGAACCTTACC AAGTCTTGACATCCCGATGACAGAACATGTAATGTGTTTTCTC TTCGGAGCATCGGTGAC | 5 |

TABLE 3-continued

| Strain name | Name | Sequence | SEQ ID NO |
|---|---|---|---|
| | | AGGTGGTGCATGGTTGTCGTCAGCTCGTGTCGTGAGATGTTGG GTTAAGTCCCGCAACGA GCGCAACCCCTATTCTTAGTAGCCAGCGGGTAAGCCGGGCAC TCTAGGGAGACTGCCAGG GATAACCTGGAGGAAGGTGGGGATGACGTCAAATCATCATGC CCCTTATGACTTGGGCTA CACACGTGCTACAATGGCGTAAACAAAGGGAAGCGAGCCTGC GAGGGGGAGCAAATCTCA AAAATAACGTCTCAGTTCGGACTGCAGTCTGCAACTCGACTG CACGAAGCTGGAATCGCT AGTAATCGCGAATCAGAATGTCGCGGTGAATACGTTCCCGGG TCTTGTACACACCGCCCG TCACACCATGGGAGTTGGTAATGCCCGAAGTCAGTGACCCAA CCGCAAGGAGGG | |

The isolated strain was named as *Roseburia intestinalis* SNUG30017, and was deposited to Korean Collection for Type Culture, and was given the accession number KCTC13327BP (*Roseburia intestinalis* SNUG30017, deposited on Sep. 1, 2017).

For a long term storage of the purely isolated and identified strain, glycerol (60% v/v) was added to the culture which reached the exponential phase to make a stock and store it at −80° C.

Example 7. Characteristic of Strengthen Tight Junction of Membrane Between Intestinal Epithelial Cells of *Roseburia* sp. Strain Caco-2 cell line was distributed from American Type Culture Collection (ATCC) and used as an animal cell for the test of the characteristic of strengthen the tight junctions of membrane between intestinal epithelial cells. The Caco-2 cell line was a human large intestine-derived colorectal cancer adenocarcinoma cell, and its form was an epithelial cell.

The Caco-2 cell was cultured at 37° C. under the presence of 5% $CO_2$ using MEM (Thermo Fisher Scientific, USA) media in which 20% fetal bovine serum (FBS), 1% non-essential amino acids solution, 1% HEPES, 1.5% sodium bicarbonate solution, penicillin-streptomycin (10 U/ml) were added. For the experiment of tight junctions of the wall between intestinal epithelial cells, the Caco-2 cell was aliquoted to a 24 trans well-plate (pore size 0.4 µm, Corning, USA) so as to be the number of $3\times10^5$ cell/ml per well, and the media was replaced every other day, and it was cultured for 7 days to completely form a monolayer to use for the experiment.

As the experimental group, *Roseburia intestinalis* SNUG30017 strain (Ri) was used, and for the control group, *Roseburia hominis* DSM 16839 strain (Rh) was distributed from Deutsche Sammlung von Mikroorganismen and Zellkulturen GmbH (DSMZ) and used. Each bacterium was cultured at 37° C. under the anaerobic condition in YBHI liquid media so as to reach the exponential phase and then was centrifuged, and then it was prepared by removing the supernatant and diluting it in PBS. For the strains, the number of bacteria was measured using Accuri C6 Flow cytometer device of BD company using a bacteria count kit. For the Caco-2 cell which formed the monolayer, media in which fetal bovine serum and antibiotics were not added were added before treating the strain, and the strain was added so that the multiplicity of infection (MOI) was 100.

Then, TransEpithelial Electrical Resistance (TEER) after 0 hour, 12 hours and 24 hours was measured.

The result was shown in FIG. 8a, and it was shown that the Ri strain increased the TransEpithelial Electrical Resistance compared to the control group, and it significantly increased the TransEpithelial Electrical Resistance compared to the control group, more in 24 hours than 12 hours. There was no significant difference in Rh compared to the control group.

Through the result, it could be seen that the *Roseburia intestinalis* SNUG30017 strain secured by isolating in Example 6 had an effect of strengthening the binding between intestinal epithelial cells and through this effect, it could alleviate alcoholic fatty liver disease symptoms.

Example 8. Characteristic of Strengthening Tight Junction of Membrane Between Intestinal Epithelial Cells of *Roseburia* sp. Strain Flagella 8-1: Extraction of flagella of *Roseburia* sp. strain To extract flagella of the *Roseburia* sp. strain, the following was performed.

The *Roseburia intestinalis* SNUG30017 strain (Ri) and *Roseburia hominis* DSM 16839 strain (Rh) were cultured at 37° C. under the anaerobic condition for 24 hours in 500 ml YBHI liquid media, and then were centrifuged at 4° C., 4,000×g for 20 minutes, and the supernatant was removed. Then, the strains were suspended in 4° C. PBS and then were homogenized for 30 seconds 3 times. This was centrifuged at 4° C., 10,000×g for 20 minutes to secure only the supernatant, and the pellet concentrated by superhigh speed centrifugation of this at 4° C., 100,000×g for 1 hour was suspended in 500 µl tertiary sterile distilled water, and the protein extracted likewise was estimated as flagella.

8-2: Confirmation of Flagella of *Roseburia* sp. Strain

The protein extract obtained in Example 8-1 was analyzed using PAGE gel, and LTQ-Orbitrap mass spectrometer.

Specifically, the protein extract derived from Ri and Rh strains was quantified using BCA protein assay kit (Thermo Fisher Scientific). The same amount was added in Laemmli sample loading buffer (Bio-Rad) comprising 10% β-mercaptoethanol, and then it was boiled at 85° C. for 10 minutes, and then it was loaded on 10% SDS-PAGE gel, thereby confirming a band in an about 35 kDa size, and the result was shown in FIG. 8b.

The band with the corresponding size was under trypsin digestion to conduct LTQ-Orbitrap mass spectrometry. As the result of matching the secured amino acid sequence with protein database secured by NCBI, it was confirmed that the extracted protein was flagella of the *Roseburia* sp. strain, and the result was shown in FIG. 8c.

In addition, for confirmation of flagella of Ri and Rh strains, after culturing in YBHI solid media at 37° C. under the anaerobic condition for 24 hours, the strains were on the grid to conduct negative staining using PTA (phosphotungstic acid). The flagella were observed by a transmission electron microscope (TEM), and the result was shown in FIG. 8d.

8-3: Confirmation of Characteristic of Tight Junctions Between Intestinal Epithelial Cells of *Roseburia* sp. Strain Flagella To confirm that the *Roseburia* sp. strain-derived flagella had the characteristic of tight junctions of membrane between intestinal epithelial cells, the following was performed.

Specifically, the Caco-2 cell line was distributed from American Type Culture Collection (ATCC) and used as an animal cell for the test of protecting tight junctions of membrane between intestinal epithelial cells destroyed by ethanol. The Caco-2 cell was cultured at 37° C. under the presence of 5% $CO_2$ using MEM (Thermo Fisher Scientific, USA) media in which 20% fetal bovine serum (FBS), 1% non-essential amino acids solution, 1% HEPES, 1.5% sodium bicarbonate solution, penicillin-streptomycin (10 U/ml) were added. For the experiment of protecting tight junctions of the wall between intestinal epithelial cells, the Caco-2 cell was aliquoted to a 24 trans well-plate (pore size 0.4 μm, Corning, USA) so as to be the number of $3 \times 10^5$ cell/ml per well, and the media was replaced every other day, and it was cultured for 7 days to completely form a monolayer to use for the experiment.

As the experimental group, *Roseburia intestinalis* SNUG30017 strain (Ri) was used, and for the control group, *Roseburia hominis* DSM 16839 strain (Rh) was distributed from Deutsche Sammlung von Mikroorganismen and Zellkulturen GmbH (DSMZ) and used. Each bacterium was cultured at 37° C. under the anaerobic condition in YBHI liquid media so as to reach the exponential phase and then was centrifuged, and then it was prepared by removing the supernatant and diluting it in PBS. For the strains, the number of bacteria was measured using Accuri C6 Flow cytometer device of BD company using a bacteria count kit. For the culture, the supernatant was treated with a 0.22 μm filter. For the flagella extracted in Example 8-1, the protein concentration was measured using BCA kit of Thermo company. The Caco-2 cell which formed the monolayer was added by media in which fetal bovine serum and antibiotics were not added before treating the strain. Each strain was added so as to be $1 \times 10^8$ cells/well, $1 \times 10^9$ cells/well, and the culture of each strain and the flagella of each strain were added 250 μM, and 500 μM, respectively.

Then, the TransEpithelial Electrical Resistance (TEER) after 0 hour and 24 hours was measured. Then, ethanol was treated by 500 mM/well, and it was cultured for 3 hours, and then the TransEpithelial Electrical Resistance was measured, and FITC permeability was measured through fluorescence.

The result of measuring the TransEpithelial Electrical Resistance in 24 hours after adding bacterial, culture and flagella was shown in FIG. 8e. In case of bacteria, it was shown that the Rh strain significantly increased the TransEpithelial Electrical Resistance compared to the control group when treated by $1 \times 10^9$ cells/well. In case of flagella, all the Ri and Rh-derived flagella significantly increased the TransEpithelial Electrical Resistance compared to the control group when added by 250 μM or 500 μM. In case of culture, it was shown that when the Ri-derived culture was treated by 1%, the TransEpithelial Electrical Resistance was significantly reduced compared to the control group. Through the above results, it could be seen that the *Roseburia* sp. strain-derived flagella had an effect of strengthening the binding between intestinal epithelial cells compared to the strain or culture.

Then, the result of measuring the TransEpithelial Electrical Resistance after treating ethanol by 500 mM/well and culturing for 3 hours was shown in FIG. 8f. As a result, it was shown that the positive control group treated by ethanol (E) very significantly reduced the TransEpithelial Electrical Resistance compared to the negative control group treated by PBS. In addition, the Ri strain significantly increased the TransEpithelial Electrical Resistance compared to the positive control group when treated by $1 \times 10^9$ cells/well. In case of culture, when the Ri-derived culture was treated by 1%, it significantly increased it compared to the positive control group, and the same result was shown in the control group treated by butyrate (but). Through the above results, it could be seen that ethanol destroyed the membrane between intestinal epithelial cells, and the Ri-derived strain and culture had an effect of protecting the binding between intestinal epithelial cells.

The result of measuring FITC permeability through fluorescence after treating FITC-dextran (Fluorescein-dextran) by 1 g/l and culturing for 1 hour was shown in FIG. 8g. As a result, it was shown that the positive control group treated by ethanol very significantly increased the permeability of the epithelial cell membrane compared to the negative control group treated by PBS. In addition, the Ri strain significantly reduced the permeability of epithelial cell membrane compared to the positive control group when treated by $1 \times 10^9$ cells/well. In case of flagella, the Ri significantly reduced the permeability of the epithelial cell membrane compared to the positive control group when added by 250 μM or 500 μM, and the Rh had a significant effect when added by 500 μM. The culture did not have an effect of reducing the permeability in all cases. Through the above results, it could be seen that the permeability was increased as the membrane between intestinal epithelial cells was destroyed by ethanol, and the Ri-derived strain and flagella had an effect of protecting the binding between intestinal epithelial cells, thereby reducing the permeability.

Example 9. Animal Experiment Model Establishment

To investigate the causal relationship between changes in gut microbiota by single strain administration and alcoholic fatty liver, an animal experiment was conducted.

Lieber DeCarli feed was administered into male 8-10 weeks C57BL/6J mice daily to induce alcoholic fatty liver. As shown in FIG. 9a, after feeding feed without alcohol for 2 days for adaptation of liquid diet, from the 3rd day, the concentration of alcohol was increased 1% and 3% per 2 days, and it was administered so as to be 5% (v/v) at the 6th day, and then after feeding 5% (v/v) for 10 days, in the morning at the 16th day, 31.5% (v/v) ethanol was orally administered, and in 9 hours, the experiment was finished. Then, for the negative control group, 45% (v/v) maltodextrin with the same calorie was orally administered. For the diet of the experimental group, by adjusting the amount of maltodextrin in addition to alcohol addition, it was made same with the calorie of the diet of the negative control group without addition of alcohol. As the experimental group, *Roseburia intestinalis* SNUG30017 (Ri) and *Roseburia hominis* DSM 16839 strain (Rh), and as the control group, *Akkermansia muciniphila* ATCC BAA-835, and *Lactobacillus rhamnosus* GG KCTC 5033 strains which were conventionally known to have an effect of alleviating alcoholic fatty liver disease were used. Each strain was colonized by the method of oral administration in an amount of $2 \times 10^9$ CFU/0.2 ml daily for 15 days, and for the negative and positive control groups, PBS was orally administrated. The weight of mice was measured at a week interval, and the feed intake was measured at an interval of 2 days, and the result was shown in FIG. 9b.

As a result, as could be seen in FIG. 9b, it was confirmed that the weight change of the ethanol group (EtOH) was significantly reduced in the positive control group compared to the negative control group (Pair), even though there was no difference in average food intake during the experimental period. This means that the weight was reduced due to ethanol despite of intake of the same calorie. There was no significant difference in weights of the ethanol group (EtOH) and *Roseburia* strain administration group (EtOH+Ri, EtOH+Rh), and in the control group, *Akkermansia muciniphila* group (EtOH+Akk), the significant reduction of the weight was caused compared to the ethanol group.

After the experiment was over, mice were sacrificed and liver, cecum and spleen were extracted and then their weighs were measured, and the result was shown in FIG. 10.

As a result, as could be seen in FIG. 10, the significant changes of the relative ratio of the liver, cecum and spleen to the body weight were shown only between the negative control group (Pair) and the positive control group, the ethanol group (EtOH), and this means that the administration of each strain did not affect the weight changes of liver, cecum and spleen.

Example 10. Confirmation of Alcoholic Fatty Liver Disease Improvement Effect of *Roseburia* Strain 10-1: Quantitative Analysis At the End of the Experiment of Example 9, the Blood of Mice was Collected, and the blood alanine aminotransferase (ALT), lipopolysaccharides (LPS) composing the cell wall of gram-negative bacteria and aspartate aminotransferase (AST) were measured. In addition, triglycerides (TG) in liver was measured, and just before finishing the experiment, dextran (4 kDa) with fluorescein isothiocyanate (FITC) fluorescence was orally administrated (60 mg/100 g body weight), and in 4 hours, blood was collected and in vivo permeability (FITC) measuring fluorescence in blood was conducted. The result was shown in FIG. 11.

As a result, as could be seen in FIG. 11, it was confirmed that in the positive control group, the ethanol group, the blood ALT concentration was significantly increased, and the alcoholic fatty liver disease was induced. In addition, in the experimental groups, *Roseburia intestinalis* SNUG30017 (Ri) and *Roseburia hominis* DSM 16839 strain (Rh), and the control group, *Akkermansia muciniphila* (Akk), the significant reduction of the blood ALT concentration occurred. ALT is a representative biomarker used as an index of liver damage, and this result means that the strain administration alleviated alcoholic fatty liver.

In case of AST, it was confirmed that in the positive control group, the ethanol group, compared to the negative control group, the blood AST concentration was significantly increased, thereby inducing alcoholic fatty liver. In addition, in the experimental group, *Roseburia intestinalis* SNUG30017 (Ri), compared to the ethanol group, the significantly reduction of the blood AST concentration occurred. AST is also a representative biomarker used as an index of liver damage, and this result means that the strain administration alleviated alcoholic fatty liver.

In case of liver triglycerides (TG), it was confirmed that in the positive control group, the ethanol group, compared to the negative control group, the triglyceride concentration in liver was significantly increased, and the alcoholic fatty liver disease was induced. In addition, in the experimental group, *Roseburia intestinalis* SNUG30017 (Ri), compared to the ethanol group, the significant reduction of triglycerides occurred, and this result means that the strain administration alleviated alcoholic fatty liver.

In case of FITC, it was confirmed that in the positive control group, the ethanol group, compared to the negative control group, the blood FITC fluorescence expression was significantly increased, and the barrier permeability which is one of causes of occurrence of alcoholic fatty liver disease was increased. In addition, in the experimental groups, *Roseburia intestinalis* SNUG30017 (Ri) and *Roseburia hominis* DSM 16839 strain (Rh), and the control group, *Akkermansia muciniphila* (Akk), compared to the ethanol group, the significant reduction of blood FITC fluorescence expression occurred, and this result means that the strain administration lowered the barrier permeability and helped alleviation of alcoholic fatty liver.

In case of LPS, one of causes of occurrence of alcoholic fatty liver, it was confirmed that in the positive control group, the ethanol group, compared to the negative control group, the concentration of blood lipopolysaccharides (LPS) was significantly increased, and the barrier permeability was increased, thereby increasing LPS derived from the intestine. In addition, in the experimental groups, *Roseburia intestinalis* SNUG30017 (Ri) and *Roseburia hominis* DSM 16839 strain (Rh), compared to the ethanol group, the significant reduction of blood LPS concentration occurred, and this result means that the strain administration intensified the barrier and that reduced the release of LPS, thereby helping alleviation of alcoholic fatty liver.

10-2: Histological Analysis

The result of conducting hematoxylin & eosin (H&E) staining, after fixing liver tissue with 10% formalin for histopathological observation was shown in in FIG. 12, and the result of conducting Oil Red O staining that is the criterion of damage of liver tissue and the result of quantifying it using ImageJ software were shown in FIG. 13a and FIG. 13b.

According to the result of FIG. 12, it was confirmed that in the positive control group, the ethanol group (II. EtOH), compared to the negative control group (I. Pair), infiltration of immunocytes such as neutrophils around central vein (CV) in addition to fat accumulation occurred. In addition, in the experimental groups, *Roseburia intestinalis* SNUG30017 (III. EtOH+Ri) and *Roseburia hominis* DSM 16839 strain (IV. EtOH+Rh), compared to the ethanol group, reduction of infiltration of immunocytes occurred, and this result means that the administration of *Roseburia* strain reduced inflammatory reactions causing alcoholic fatty liver.

According to the results of FIG. 13a and FIG. 13b, in the positive control group, the ethanol group (II. EtOH), the enlarged fat accumulation in liver was confirmed, but in the Ri (III. EtOH+Ri) and Rh (IV. EtOH+Rh) strains-administered experimental groups, it was confirmed that the fat accumulation in liver was alleviated. In particular, as the result of quantifying red in the randomly selected 6 regions, it was confirmed that it was significantly reduced (FIG. 13b). FIG. 13b is the result of quantifying red showing fat using ImageJ program, by securing 6 photographs of Oil Red O staining results of the randomly selected regions.

10-3: Gene Expression Analysis

For analysis of gene expression of tissue, RNA of liver tissue was extracted using RNeasy Lipid tissue mini kit (Qiagen), and RNA of intestine tissue was extracted using easy-spin total RNA extraction kit (Intron). The result of analyzing gene expression using roter-gene SYBR green PCR kit (Qiagen) after synthesizing them into cDNA using high capacity RNA-to-cDNA kit (Applied biosystems) was shown in FIG. 14 (liver tissue) and FIG. 15a (intestine tissue).

FIG. 14 is the comparison analysis of expression of PPAR-γ and CD36 that are genes related to fat metabolism such as triglyceride synthesis and fatty acid transport in liver, and gene expression of CXCL2 and CXCL5 that are chemokines activating neutrophil recruitment, and expression of TNF-α and IL-1β known as inflammatory cytokines.

FIG. 15a is the comparison analysis of gene expression of Zo-1, Occludin that are related to tight junctions between intestinal epithelial cells in the intestine, and gene expression of MUC2 related to the mucus layer.

Then, the primers (SEQ ID NOs: 6 to 27) of the following Table 4 were used, and the expression of liver and intestine was corrected by 18S and HPRT house keeping gene, respectively.

TABLE 4

| Classification | SEQ ID NO: | Target gene | Sequence (5'->3') |
|---|---|---|---|
| Forward | 6 | 18S | GTAACCCGTTGAACCCCATT |
| Reverse | 7 | 18S | CCATCCAATCGGTAGTAGCG |
| Forward | 8 | Ppar-γ | ATGTCTCACAATGCCATCAGGTT |
| Reverse | 9 | Ppar-γ | GCTCGCAGATCAGCAGACTCT |
| Forward | 10 | CD36 | TTGTACCTATACTGTGGCTAAATGAGA |
| Reverse | 11 | CD36 | CTTGTGTTTGAACATTTCTGCTT |
| Forward | 12 | CXCL2 | AAAGTTTGCCTTGACCCTGAA |
| Reverse | 13 | CXCL2 | CTCAGACAGCGAGGCACATC |
| Forward | 14 | CXCL5 | TGATCCCTGCAGGTCCACA |
| Reverse | 15 | CXCL5 | CTGCGAGTGCATTCCGCTTA |
| Forward | 16 | TNF-α | CATCTTCTCAAAATTCGAGTGACAA |
| Reverse | 17 | TNF-α | TGGGAGTAGACAAGGTACAACCC |
| Forward | 18 | IL-1β | GAAATGCCACCTTTTGACAGTG |
| Reverse | 19 | IL-1β | CTGGATGCTCTCATCAGGACA |
| Forward | 20 | Zo-1 | ACCCGAAACTGATGCTGTGGATAG |
| Reverse | 21 | Zo-1 | AAATGGCCGGGCAGAACTTGTGTA |
| Forward | 22 | Occludin | GGAGGACTGGGTCAGGGAATA |
| Reverse | 23 | Occludin | CGTCGTCTAGTTCTGCCTGT |
| Forward | 24 | MUC2 | ACTGCACATTCTTCAGCTGC |
| Reverse | 25 | MUC2 | ATTCATGAGGACGGTCTTGG |
| Forward | 26 | HPRT | TTATGGACAGGACTGAAAGAC |
| Reverse | 27 | HPRT | GCTTTAATGTAATCCAGCAGGT |

According to the result of FIG. 14, the expression of PPAR-γ and CD36 was significantly increased in the positive control group (EtOH) compared to the negative control group (Pair), and this means the increase of fat metabolism in liver by ethanol. On the other hand, in the Ri strain-administered experimental group (EtOH+Ri), compared to the positive control group, the expression of both genes was significantly reduced, and in the Rh-administered experimental group (EtOH+Rh), the CD36 expression was significantly reduced. This means that the administration of the Roseburia strain reduced the expression of genes related to fat metabolism, thereby helping alleviation of alcoholic fatty liver.

In addition, in the positive control group (EtOH), compared to the negative control group (Pair), the expression of CXCL2 and CXCL5 was significantly increased, and this means the increase of inflammatory reactions and increase of immunocyte activity in liver by ethanol. In particular, CXCL2 and CXCL5 are chemokines that are one of inflammatory cytokines, and induce inflammation. On the other hand, in the Ri-administered experimental group (EtOH+Ri), compared to the positive control group, the expression of both genes was significantly reduced, and the Rh-administered experimental group (EtOH+Rh), the expression of CXCL2 was significantly reduced. This means that the administration of the Roseburia strain reduced the expression of genes related to immunocyte regulation, thereby helping alleviation of alcoholic fatty liver.

Furthermore, the expression of TNF-α and IL-1β was significantly increased in the positive control group (EtOH) compared to the negative control group (Pair), and this means the increase of inflammatory reactions in liver by ethanol. On the other hand, both were significantly reduced in the Ri and Rh-administered experimental groups (EtOH+Ri, EtOH+Rh), and this means the reduction of inflammatory reactions in liver by strain administration.

According to the result of FIG. 15a, in case of Zo-1, there was no significant difference between the negative control group (Pair) and positive control group (EtOH). On the other hand, in case of Occludin, the expression was significantly reduced in the positive control group (EtOH) compared to the negative control group (Pair), and this means that the Occludin expression affects the reduction of tight junctions between intestinal epithelial cells in the intestine by ethanol. Meanwhile, in all the Ri and Rh-administered experimental groups (EtOH+Ri, EtOH+Rh) and the Akk-administered control group (EtOH+Akk), the Occludin expression was significantly increased. This means that the administration of the Roseburia strain increased the Occludin expression and strengthened the membrane between intestinal epithelial cells, thereby helping alleviation of alcoholic fatty liver.

In case of MUC2, the expression was significantly reduced in the positive control group (EtOH) compared to the negative control group (Pair), and this means that the permeability of the mucus layer was more increased by ethanol. On the other hand, in all the Ri and Rh-administered experimental groups (EtOH+Ri, EtOH+Rh), the MUC2 expression was significantly increased. This means that the administration of the Roseburia strain increased the MUC2 expression and strengthened the mucus layer, thereby helping alleviation of alcoholic fatty liver.

10-4: Protein Expression Analysis

For analysis of protein expression of intestine tissue, the protein of intestine tissue was homogenized in protease inhibitor cocktail-added RIPA buffer and was extracted, and then it was quantified using BCA protein assay kit (Thermo Fisher Scientific). Laemmli sample loading buffer (Bio-Rad)

comprising 10% β-mercaptoethanol was added, and it was boiled at 85° C. for 10 minutes, and then 10% SDS-PAGE gel was conducted. Then, the membrane was blocked in 5% BSA-added TBST for 1 hour, and then primary and secondary antibodies were attached, to progress the reaction. The reaction intensity was quantified by GeneTools (Syngene).

FIG. 15b shows the protein expression of Occludin related to tight junctions between intestine epithelial cells in intestine and β-actin that is a house keeping gene, and FIG. 15c is a graph showing the relative protein expression by quantifying the result obtained from 4-5 samples in total per group and correcting by β-actin value. According to the results of FIG. 15b and FIG. 15c, the expression of Occludin was significantly reduced in the positive control group (EtOH) compared to the negative control group (Pair), and this means that the membrane between intestine epithelial cells becomes weaker due to reduction of Occludin expression in the intestine by ethanol. On the other hand, in all the Ri and Rh-administered experimental groups (EtOH+Ri, EtOH+Rh) and Akk-added control group (EtOH+Akk), the Occludin expression was significantly increased, and Ri increased the expression most significantly. In particular, this means that the administration of the *Roseburia intestinalis* strain increased the Occludin expression and strengthened the membrane between intestine epithelial cells, thereby helping alleviation of alcoholic fatty liver.

10-5: Analysis of Gut Microbiota Using 16S rRNA

At the end of the experiment of Example 9, the cecum of mice was collected and was stored frozen at −81° C., and the sample was moved to the laboratory and bacteria genomic DNA was extracted using QIAamp FAST DNA stool mini kit (Qiagen). The extracted DNA was amplified using primers (SEQ ID NOs: 28 and 29) of the following Table 5 targeting V3-4 regions of bacterial 16S rRNA gene, and after performing index PCR, sequence data were produced using MiSeq device of Illumina company. The produced bulk sequence was analyzed using QIIME pipeline, and the structure of gut microbiota was identified by confirming the whole genome information of gut microbiota, and then the univariate analysis by group (LefSE) was conducted.

TABLE 5

| Classification | SEQ ID NO: | Nucleic acid sequence (5'->3') |
|---|---|---|
| Forward | 28 | TCGTCGGCAGCGTCAGATGTGTATA AGAGACAGCCTACGGGNGGCWGCAG |
| Reverse | 29 | GTCTCGTGGGCTCGGAGATGTGTATA AGAGACAGGACTACHVGGGTATCTAA TCC |

The result of confirming the changes in diversity of gut microbiota analyzed on the basis of 16S rRNA by group with Faith's Phylogenetic diversity and Chao1 indexes was shown in FIG. 16a and FIG. 16b, and in case of Faith's Phylogenetic diversity index, it was confirmed that the diversity of gut microbiota was significantly reduced in the positive control group, the ethanol group, compared to the negative control group. This suggests that the increase of alcohol intake may negatively affect the intestine health, due to reduction of beneficial bacteria and dominance of potential harmful bacteria. On the other hand, in the Ri and LGG-administered experimental groups, two indexes showed that the diversity of gut microbiota was significantly increased. This suggests that the strain administration may increase the diversity of gut microbiota, thereby positively affecting the intestine health.

As the result of conducting analysis of major components of gut microbiota analyzed on the basis of 16S rRNA was shown in FIG. 16c, and through PCA plot, it was confirmed that the positive control group, the ethanol group had a very different structure of gut microbiota from the negative control group. On the other hand, it was confirmed that only the Ri-administered experimental group had the different gut microbiota structure from the positive control group, the ethanol group. This suggests that the strain administration changed species consisting of gut microbiota, thereby modulating its structure.

To analyze which gut microbiota is changed, the result of conducting the univariate analysis (LefSE) was shown in FIG. 16d. In the positive control group, the ethanol group, the dominance of the representative harmful bacterium, Enterobacteriaceae of which cell wall consists of lipopolysaccharides (LPS) was confirmed. On the other hand, in the Ri-administered experimental group, the increase of *Akkermansia* and *Prevotella* was confirmed. This means that the strain administration changed this gut microbiota, thereby helping alleviation of alcoholic fatty liver.

The result of conducting gut microbiota KEFF pathways function estimation analysis through PICRUSt was shown in FIG. 17. In the positive control group, the ethanol group, the dominance of glycan degradation and galactose metabolic function was confirmed. On the other hand, in the Ri-administered experimental group, the increase of DNA repair and metabolic function was confirmed. This means that the strain administration controlled the function of gut microbiota, helping alleviation of alcoholic fatty liver.

The invention claimed is:

1. A composition in the form of a tablet comprising an amount of *Roseburia intestinalis* SNUG30017 strain having the accession number KCTC13327BP.

2. The composition of claim 1, wherein the amount is $2 \times 10^9$ CFU of the *Roseburia intestinalis* SNUG30017 strain.

3. The composition according to claim 1, wherein the composition is a probiotic composition.

4. The composition according to claim 1, further comprising at least one of a pharmaceutically acceptable excipient and a freeze-drying agent.

5. The composition of claim 1, wherein the *Roseburia intestinalis* SNUG30017 strain comprises flagella and the strain has one or more characteristics of strengthening tight junctions between epithelial cells, reducing the concentration of blood lipopolysaccharide (LPS), increasing expression of Occludin gene, and increasing expression of MUC2 gene in a mammal orally administered with the composition compared to a corresponding mammal not administered with the composition in an alcoholic fatty liver disease-induced animal model.

6. The composition of claim 1, wherein the *Roseburia intestinalis* SNUG30017 strain comprises flagella and the strain has the characteristic of reducing expression of at least one of CXCL2, CXCL5, TNF-alpha, and IL-1 beta liver inflammatory cytokine genes, or at least one of PPAR-gamma and CD36 liver fat synthesis genes in a mammal orally administered with the composition compared to a corresponding mammal not administered with the composition in an alcoholic fatty liver disease-induced animal model.

7. The composition of claim 1, wherein the *Roseburia intestinalis* SNUG30017 strain comprises flagella and the strain has the characteristic of reducing concentration of at least one of blood alanine aminotransferase (ALT), blood aspartate aminotransferase (AST), and liver triglycerides in a mammal orally administered with the composition compared to a corresponding mammal not administered with the composition in an alcoholic fatty liver disease-induced animal model.

8. A pharmaceutical composition in the form of a tablet comprising one or more of cells of the *Roseburia intestinalis* SNUG30017 strain having the accession number KCTC13327BP, a flagella extract of the strain comprising a flagellin, a culture of the strain, and a concentrate and dried product of the culture.

9. A food composition in the form of a dairy product, yogurt, curd, cheese, fermented oil, powdered milk, a milk-based fermented product, ice cream, a fermented cereal-based product, milk based powder, a beverage, a dressing, or a pet feed comprising one or more of cells of *Roseburia intestinalis* SNUG30017 strain having the accession number KCTC13327BP, a flagella extract of the strain comprising a flagellin, a culture of the strain, and a concentrate and dried product of the culture.

10. The composition according to claim 9, wherein the food composition is a probiotic composition.

11. The composition according to claim 9, wherein the *Roseburia intestinalis* SNUG30017 strain causes an increase of *Akkermansia* and *Prevotella* in the gut microbiota of a mammal orally administered with the composition compared to a corresponding mammal not administered with the composition in an alcoholic fatty liver disease-induced animal model.

* * * * *

SEQUENCE LISTING

<160> NUMBER OF SEQ ID NOS: 29

<210> SEQ ID NO 1
<211> LENGTH: 59
<212> TYPE: DNA
<213> ORGANISM: Artificial Sequence
<220> FEATURE:
<223> OTHER INFORMATION: (synthetic) primer 515F

<400> SEQUENCE: 1
atgatacggc gaccaccgag atctacacta tggtaattgt gtgccagcmg ccgcggtaa        59

<210> SEQ ID NO 2

```
<211> LENGTH: 56
<212> TYPE: DNA
<213> ORGANISM: Artificial Sequence
<220> FEATURE:
<223> OTHER INFORMATION: (synthetic) primer 806R

<400> SEQUENCE: 2
caagcagaag acggcatacg agatagtcag tcagccggac tachvgggtw tctaat      56

<210> SEQ ID NO 3
<211> LENGTH: 20
<212> TYPE: DNA
<213> ORGANISM: Artificial Sequence
<220> FEATURE:
<223> OTHER INFORMATION: (synthetic) primer 27F

<400> SEQUENCE: 3
agagtttgat ymtggctcag                                              20

<210> SEQ ID NO 4
<211> LENGTH: 21
<212> TYPE: DNA
<213> ORGANISM: Artificial Sequence
<220> FEATURE:
<223> OTHER INFORMATION: (synthetic) primer 1492R

<400> SEQUENCE: 4
tacggytacc ttgttacgac t                                            21

<210> SEQ ID NO 5
<211> LENGTH: 1434
<212> TYPE: DNA
<213> ORGANISM: Artificial Sequence
<220> FEATURE:
<223> OTHER INFORMATION: Rosebuia intestinalis

<400> SEQUENCE: 5
ttatggctca ggatgaacgc tggcggcgtg cttaacacat gcaagtcgaa cgaagcactt      60
tatttgattt cttcggaatg aagattttgt gactgagtgg cggacgggtg agtaacgcgt     120
gggtaacctg cctcatacag ggggataaca gttggaaacg actgctaata ccgcataagc     180
gcacagggtc gcatgacctg gtgtgaaaaa ctccggtggt atgagatgga cccgcgtctg     240
attagccagt tggtggggta acggcctacc aaagcgacga tcagtagccg acctgagagg     300
gtgaccggcc acattgggac tgagacacgg cccaaactcc tacgggaggc agcagtgggg     360
aatattgcac aatgggggaa accctgatgc agcgacgccg cgtgagcgaa gaagtatttc     420
ggtatgtaaa gctctatcag cagggaagaa gaaatgacgg tacctgacta agaagcaccg     480
gctaaatacg tgccagcagc cgcggtaata cgtatggtgc aagcgttatc cggatttact     540
gggtgtaaag ggagcgcagg cggtacggca agtctgatgt gaaagcccgg ggctcaaccc     600
cggtactgca ttggaaactg tcggactaga gtgtcgagg ggtaagtgga attcctagtg     660
tagcggtgaa atgcgtagat attaggagga acaccagtgg cgaaggcggc ttactggacg     720
attactgacg ctgaggctcg aaagcgtggg gagcaaacag gattagatac cctggtagtc     780
cacgccgtaa acgatgaata ctaggtgtcg gggagcattg ctcttcggtg ccgcagcaaa     840
cgcaataagt attccacctg gggagtacgt tcgcaagaat gaaactcaaa ggaattgacg     900
gggacccgca caagcggtgg agcatgtggt ttaattcgaa gcaacgcgaa gaaccttacc     960
aagtcttgac atcccgatga cagaacatgt aatgtgtttt ctcttcggag catcggtgac    1020
aggtggtgca tggttgtcgt cagctcgtgt cgtgagatgt tgggttaagt cccgcaacga    1080
```

```
gcgcaacccc tattcttagt agccagcggg taagccgggc actctaggga gactgccagg    1140
gataacctgg aggaaggtgg ggatgacgtc aaatcatcat gccccttatg acttgggcta    1200
cacacgtgct acaatggcgt aaacaaaggg aagcgagcct gcgaggggga gcaaatctca    1260
aaaataacgt ctcagttcgg actgcagtct gcaactcgac tgcacgaagc tggaatcgct    1320
agtaatcgcg aatcagaatg tcgcggtgaa tacgttcccg ggtcttgtac acaccgcccg    1380
tcacaccatg ggagttggta atgcccgaag tcagtgaccc aaccgcaagg aggg          1434
```

```
<210> SEQ ID NO 6
<211> LENGTH: 20
<212> TYPE: DNA
<213> ORGANISM: Artificial Sequence
<220> FEATURE:
<223> OTHER INFORMATION: (synthetic) 18S-FWD primer

<400> SEQUENCE: 6
gtaacccgtt gaacccattt                                                  20
```

```
<210> SEQ ID NO 7
<211> LENGTH: 20
<212> TYPE: DNA
<213> ORGANISM: Artificial Sequence
<220> FEATURE:
<223> OTHER INFORMATION: (synthetic) 18S-REV primer

<400> SEQUENCE: 7
ccatccaatc ggtagtagcg                                                  20
```

```
<210> SEQ ID NO 8
<211> LENGTH: 23
<212> TYPE: DNA
<213> ORGANISM: Artificial Sequence
<220> FEATURE:
<223> OTHER INFORMATION: (synthetic) Ppar-r FWD primer

<400> SEQUENCE: 8
atgtctcaca atgccatcag gtt                                              23
```

```
<210> SEQ ID NO 9
<211> LENGTH: 21
<212> TYPE: DNA
<213> ORGANISM: Artificial Sequence
<220> FEATURE:
<223> OTHER INFORMATION: (synthetic) Ppar-r REV primer

<400> SEQUENCE: 9
gctcgcagat cagcagactc t                                                21
```

```
<210> SEQ ID NO 10
<211> LENGTH: 27
<212> TYPE: DNA
<213> ORGANISM: Artificial Sequence
<220> FEATURE:
<223> OTHER INFORMATION: (synthetic) CD36 FWD primer

<400> SEQUENCE: 10
ttgtacctat actgtggcta aatgaga                                          27
```

```
<210> SEQ ID NO 11
<211> LENGTH: 23
<212> TYPE: DNA
<213> ORGANISM: Artificial Sequence
<220> FEATURE:
```

<223> OTHER INFORMATION: (synthetic) CD36 REV primer

<400> SEQUENCE: 11
cttgtgtttg aacatttctg ctt    23

<210> SEQ ID NO 12
<211> LENGTH: 21
<212> TYPE: DNA
<213> ORGANISM: Artificial Sequence
<220> FEATURE:
<223> OTHER INFORMATION: (synthetic) CXCL2 FWD primer

<400> SEQUENCE: 12
aaagtttgcc ttgaccctga a    21

<210> SEQ ID NO 13
<211> LENGTH: 20
<212> TYPE: DNA
<213> ORGANISM: Artificial Sequence
<220> FEATURE:
<223> OTHER INFORMATION: (synthetic) CXCL2 REV primer

<400> SEQUENCE: 13
ctcagacagc gaggcacatc    20

<210> SEQ ID NO 14
<211> LENGTH: 19
<212> TYPE: DNA
<213> ORGANISM: Artificial Sequence
<220> FEATURE:
<223> OTHER INFORMATION: (synthetic) CXCL5 FWD primer

<400> SEQUENCE: 14
tgatccctgc aggtccaca    19

<210> SEQ ID NO 15
<211> LENGTH: 20
<212> TYPE: DNA
<213> ORGANISM: Artificial Sequence
<220> FEATURE:
<223> OTHER INFORMATION: (synthetic) CXCL5 REV primer

<400> SEQUENCE: 15
ctgcgagtgc attccgctta    20

<210> SEQ ID NO 16
<211> LENGTH: 25
<212> TYPE: DNA
<213> ORGANISM: Artificial Sequence
<220> FEATURE:
<223> OTHER INFORMATION: (synthetic) TNF-a FWD primer

<400> SEQUENCE: 16
catcttctca aaattcgagt gacaa    25

<210> SEQ ID NO 17
<211> LENGTH: 23
<212> TYPE: DNA
<213> ORGANISM: Artificial Sequence
<220> FEATURE:
<223> OTHER INFORMATION: (synthetic) TNF-a REV primer

<400> SEQUENCE: 17
tgggagtaga caaggtacaa ccc    23

-continued

```
<210> SEQ ID NO 18
<211> LENGTH: 22
<212> TYPE: DNA
<213> ORGANISM: Artificial Sequence
<220> FEATURE:
<223> OTHER INFORMATION: (synthetic) IL-1b FWD primer

<400> SEQUENCE: 18
gaaatgccac cttttgacag tg                                           22

<210> SEQ ID NO 19
<211> LENGTH: 21
<212> TYPE: DNA
<213> ORGANISM: Artificial Sequence
<220> FEATURE:
<223> OTHER INFORMATION: (synthetic) IL-1b REV primer

<400> SEQUENCE: 19
ctggatgctc tcatcaggac a                                            21

<210> SEQ ID NO 20
<211> LENGTH: 24
<212> TYPE: DNA
<213> ORGANISM: Artificial Sequence
<220> FEATURE:
<223> OTHER INFORMATION: (synthetic) Zo-1 FWD primer

<400> SEQUENCE: 20
acccgaaact gatgctgtgg atag                                         24

<210> SEQ ID NO 21
<211> LENGTH: 24
<212> TYPE: DNA
<213> ORGANISM: Artificial Sequence
<220> FEATURE:
<223> OTHER INFORMATION: (synthetic) Zo-1 REV primer

<400> SEQUENCE: 21
aaatggccgg gcagaacttg tgta                                         24

<210> SEQ ID NO 22
<211> LENGTH: 21
<212> TYPE: DNA
<213> ORGANISM: Artificial Sequence
<220> FEATURE:
<223> OTHER INFORMATION: (synthetic) Occludin FWD primer

<400> SEQUENCE: 22
ggaggactgg gtcagggaat a                                            21

<210> SEQ ID NO 23
<211> LENGTH: 20
<212> TYPE: DNA
<213> ORGANISM: Artificial Sequence
<220> FEATURE:
<223> OTHER INFORMATION: (synthetic) Occludin REV primer

<400> SEQUENCE: 23
cgtcgtctag ttctgcctgt                                              20

<210> SEQ ID NO 24
<211> LENGTH: 20
<212> TYPE: DNA
<213> ORGANISM: Artificial Sequence
<220> FEATURE:
<223> OTHER INFORMATION: (synthetic) MUC2 FWD primer
```

```
<400> SEQUENCE: 24
actgcacatt cttcagctgc                                                   20

<210> SEQ ID NO 25
<211> LENGTH: 20
<212> TYPE: DNA
<213> ORGANISM: Artificial Sequence
<220> FEATURE:
<223> OTHER INFORMATION: (synthetic) MUC2 REV primer

<400> SEQUENCE: 25
attcatgagg acggtcttgg                                                   20

<210> SEQ ID NO 26
<211> LENGTH: 21
<212> TYPE: DNA
<213> ORGANISM: Artificial Sequence
<220> FEATURE:
<223> OTHER INFORMATION: (synthetic) HPRT FWD primer

<400> SEQUENCE: 26
ttatggacag gactgaaaga c                                                 21

<210> SEQ ID NO 27
<211> LENGTH: 22
<212> TYPE: DNA
<213> ORGANISM: Artificial Sequence
<220> FEATURE:
<223> OTHER INFORMATION: (synthetic) HPRT REV primer

<400> SEQUENCE: 27
gctttaatgt aatccagcag gt                                                22

<210> SEQ ID NO 28
<211> LENGTH: 50
<212> TYPE: DNA
<213> ORGANISM: Artificial Sequence
<220> FEATURE:
<223> OTHER INFORMATION: (synthetic) FWD primer
<220> FEATURE:
<221> NAME/KEY: misc_feature
<222> LOCATION: (42)
<223> OTHER INFORMATION: n is g, a, t, or c

<400> SEQUENCE: 28
tcgtcggcag cgtcagatgt gtataagaga cagcctacgg gnggcwgcag                  50

<210> SEQ ID NO 29
<211> LENGTH: 55
<212> TYPE: DNA
<213> ORGANISM: Artificial Sequence
<220> FEATURE:
<223> OTHER INFORMATION: (synthetic) REV primer

<400> SEQUENCE: 29
gtctcgtggg ctcggagatg tgtataagag acaggactac hvgggtatct aatcc            55
```